(12) United States Patent
Hefner, Jr.

(10) Patent No.: US 7,626,059 B2
(45) Date of Patent: Dec. 1, 2009

(54) MULTIFUNCTIONAL ETHYNYL SUBSTITUTED MONOMERS AND POLYARYLENE COMPOSITIONS THEREFROM

(75) Inventor: Robert E. Hefner, Jr., Lake Jackson, TX (US)

(73) Assignee: Dow Global Technologies Inc.

( * ) Notice: Subject to any disclaimer, the term of this patent is extended or adjusted under 35 U.S.C. 154(b) by 641 days.

(21) Appl. No.: 10/575,993

(22) PCT Filed: Oct. 19, 2004

(86) PCT No.: PCT/US2004/034327

§ 371 (c)(1),
(2), (4) Date: Apr. 17, 2006

(87) PCT Pub. No.: WO2005/037761

PCT Pub. Date: Apr. 28, 2005

(65) Prior Publication Data

US 2009/0012193 A1   Jan. 8, 2009

(51) Int. Cl.
*C07C 49/527* (2006.01)
*B05D 3/02* (2006.01)
*C08F 36/00* (2006.01)
*H01L 29/08* (2006.01)

(52) U.S. Cl. .............. 568/330; 427/385.5; 526/283; 526/285

(58) Field of Classification Search ............ 568/330
See application file for complete search history.

(56) References Cited

U.S. PATENT DOCUMENTS

| | | | |
|---|---|---|---|
| 4,400,540 | A | 8/1983 | Reinhardt et al. |
| 5,189,117 | A | 2/1993 | Hefner, Jr. |
| 5,270,406 | A | 12/1993 | Earls et al. |
| 5,637,669 | A | 6/1997 | Hefner, Jr. et al. |
| 5,965,679 | A | 10/1999 | Godschalx et al. |
| 6,156,812 | A | 12/2000 | Lau et al. |
| 6,172,128 | B1 | 1/2001 | Lau et al. |
| 6,359,091 | B1 | 3/2002 | Godschalx et al. |
| 6,653,358 | B2 | 11/2003 | Bruza et al. |
| 6,887,910 | B2 | 5/2005 | Bruza et al. |
| 7,381,850 | B2* | 6/2008 | Godschalx et al. .......... 568/330 |
| 2003/0027970 | A1 | 2/2003 | Haasmann et al. |
| 2003/0083392 | A1 | 5/2003 | Bruza et al. |
| 2003/0165625 | A1 | 9/2003 | So et al. |
| 2004/0053033 | A1 | 3/2004 | Niu et al. |
| 2004/0054111 | A1 | 3/2004 | Kalantar |
| 2005/0014855 | A1 | 1/2005 | Bruza |

FOREIGN PATENT DOCUMENTS

| | | |
|---|---|---|
| EP | 1245586 A2 | 10/2002 |
| WO | WO-00/31183 | 6/2000 |
| WO | WO-03/068825 A2 | 8/2003 |
| WO | WO-03/070777 A1 | 8/2003 |
| WO | WO 2004/089862 | 10/2004 |
| WO | WO-2004/090018 A1 | 10/2004 |

OTHER PUBLICATIONS

Baker, G. L. and J. K. Stille, "Hexaarylbenzene Units as Cross-Linking Sites for Polyquinolines", Macromolecules, 1979, pp. 369-373, vol. 12, No. 3.

Braham, J. N., T. Hodgins, T. Katto, R. T. Kohl, and J. K. Stille, "Polyphenylenes via Bis(2-pyrones) and Diethynylbenzenes. The Effect of m- and p- Phenlene Unites in the Chain", Macromolecules, 1978, pp. 343-346, vol. 11, No. 2.

Capek, Ignac and Jakub Chudej, "On the fine emulsion polymerization of styrene with non-ionic emulsifier," Polymer Bulletin, vol. 1999, 43, pp. 417-424.

Donescu et al., "The Influence of Monomers upon Microemulsions with Short Chain Cosurfactant," J. Dispersion Science and Technology, vol. 22, Nos. 2&3, pp. 231-244, 2001.

Feldman, Ken S., Robert E. Ruckle, Jr., Susan M. Ensel and Paul H. Weinreb, "Synthesis of a Chiral Binaphtyldisulfide: A Potentially Useful Reagent forCatalytic Asymmetric Syntheis", Tetrahedron, 1992, pp. 7101-7102, vol. 33, No. 47.

Gutsche et al., "Calixarenes. 6. Synthesis of a Functionalizable Calix[4]arene in a Conformationally Rigid Cone Conformation," J. Am. Chem. Soc., vol. 104, pp. 2652-2653 (1982).

Kraft, Amo et al., "Supramolecular liquid crystals with columnar mesophases through self-assembly of carboxylic acids around a tribasic core," Chem. Comm, pp. 1015-1016 (2000).

Kumar, Uday and Thomas X. Neenan, "Diels-Alder Polymerization between Bis(cyclopentadienones) and Acetylenes. A Versatile Route to New Hightly Aromatic Polymers", Macromolecules, 1995, pp. 124-130, vol. 28, No. 1.

Larpent, C. and T. F. Tadros, "Preparation of microlatex dispersions using oil-in-water microemulsions", Colloid Polmer Science, 1991, pp. 1171-1183, vol. 269, No. 11.

Lee, Hyung-Kun et al., "Synthesis of a Nanoporous Polymer with Hexagonal Channels from Supramolecular Discotic Liquid Crystals," Angew. Chem. Int. Ed., vol. 40, No. 14, pp. 2669-2671 (2001).

Liu, Zhi, and Jerrold Meinwald, "5-(Trimethylstannyl)-2H-pyran-2-one and 3-(Trimethylstannyl)-2H-pyran-2-one: New 2H-Pyran-2-one Synthons", J. Org. Chem., 1996, pp. 6693-6699, vol. 61, No. 19.

McDonald et al., "Diels-Alder Reactivity of Oxygenated Dienes and Furans. Synthesis of Oxygenated Bipheynyls," J. Chem. Soc. Perk. Trans., vol. 1, pp. 1893-1900, 1979.

Ogliaruso, Michael A. and Ernest I. Becker, "Bistetracyclones and Bishexaphenylbenzenes. II", J. Org. Chem., 1965, pp. 3354-3360, vol. 30.

(Continued)

Primary Examiner—Sikarl A Witherspoon

(57) ABSTRACT

A compound (monomer) comprising i) one or more arylethynyl groups (A-functional groups), ii) one or more ring structures comprising two conjugated carbon-to-carbon double bonds and a leaving group L (B-functional groups), and iii) one or more ethynyl groups (C'-functional groups), characterized in that said A- and C'-functional groups are capable of reaction under cycloaddition reaction conditions with said B-functional groups to thereby form a cross-linked, polyphenylene polymer.

8 Claims, No Drawings

OTHER PUBLICATIONS

Ogliaruso, Michael A., Lewis A. Shadoff and Ernest I. Becker, "Bistetracyclones and Bishexaphenylbenzenes", *J. Org. Chem.*, 1963, pp. 2725-2728, vol. 28.

Puetter et al., *J. Prakt. Chem.*, 1951, vol. 149, pp. 183-216.

Schilling, Jr., Curtis L., Joe A. Reed, and J. K. Stille, "Diels-Alder Polymeriztions. VI. Phenylated Polyphenylenes from Bis-2-pyrones and p-Diethynylbenzene", Macromolecules, 1969, pp. 85-88, vol. 2, No. 1.

Tong, Ling, Douglas M. Ho, Nancy J. Vogelaar, Clarence E. Schutt, and Robert A. Pascal, Jr., "The Albatrossenes: Large, Cleft-Containing, Polyphenyl Polycyclic Aromatic Hydrocarbons", J. Am. Chem. Soc., 1997, pp. 7291-7302, vol. 119, No. 31.

Turchi , Stefania, Fodolfo Nesi, and Donatella Giomi, "Reactions of 4,5-Dicyanopyridazine with Alkynes and Enamines: a New Straghtforward Complementary Route to 4-Mono- and 4,5-Disubstituted Phthalonitriles", Tetrahedron, 1998, pp. 1809-1816, vol. 54.

Vankerckhoven, Henk F., Yvan K. Gilliams, and J. K. Stille, "Poly(p-phenylene). The Reaction of 5,5'-p-Phenylenebis-2-pyrone with p-Diethynylbenzene", Macromolecules, pp. 541-546, vol. 5, No. 5, 1972.

H. Warson, *The Applications of Synthetic Resin Emulsions*, 1972, p. 88.

Wiesler, U.-M., A. J. Berresheim, F. Morgenroth, G. Lieser, and K. Müllen, "Divergent Synthesis of Polyphenylene Dendrimers: The Role of Core and Branching Reagents upn Size and Shape", Macromolecules, 2001, pp. 187-199, vol. 34, No. 2.

Zhong, Ben et al., "Porous ultra low-k dielectrics having ultra small pores", Abstracts of Papers, 224th ACS National Meeting, Boston, MA, Aug. 18-22, 2002, Published by the American Chemical Society.

Chemical Abstract 2001:404713.

Chemical Abstract 2003:570956.

Chemical Abstract 2002:566264.

Chemical Abstract 2000:133674.

Chemical Abstract 1999:184247.

Ciferri, Albert ed., *Liquid Crystallinity in Polymers: Principles and Fundamental Properties*, Chapter 8. Liquid-Crystalline Sidechain Polymers. H. Finkelmann, pp. 315-340 (1991).

\* cited by examiner

MULTIFUNCTIONAL ETHYNYL SUBSTITUTED MONOMERS AND POLYARYLENE COMPOSITIONS THEREFROM

This invention relates to compositions having at least three different reactive functional groups and to aromatic polymers made from these monomers. More particularly, the invention relates to compositions comprising in a single monomer polyphenylene matrix forming functionality comprising both arylethynyl and ethynyl functionality. The resulting polymers are useful in making low dielectric constant insulating layers in microelectronic devices.

Polyarylene resins, such as those disclosed in U.S. Pat. No. 5,965,679 (Godschalx et al.) are low dielectric constant materials suitable for use as insulating films in semiconductor devices, especially integrated circuits. Such polyarylene compounds are prepared by reacting polyfunctional compounds having two or more cyclopentadienone groups with polyfunctional compounds having two or more aromatic acetylene groups, at least some of the polyfunctional compounds having three or more reactive groups. Certain single component reactive monomers which contained one cyclopentadienone group together with two aromatic acetylene groups, specifically 3,4-bis(3-(phenylethynyl)phenyl)-2,5-dicyclopentadienone and 3,4-bis(4-(phenylethynyl)phenyl)-2,5-dicyclopentadienone, and polymers made from such monomers were also disclosed in the foregoing reference. Typically, these materials are b-staged in a solution and then coated onto a substrate followed by curing (vitrification) at elevated temperatures as high as 400-450° C. to complete the cure.

In U.S. Pat. No. 6,359,091, it was taught that it may be desirable to adjust the modulus of polymers as taught in Godschalx et al., by adjusting the ratio of the reactants or by adding other reactive species to the monomers or to the partially polymerized product of Godschalx et al. U.S. Pat. No. 6,172,128 teaches aromatic polymers containing cyclopentadienone groups that may react with aromatic polymers containing phenylacetylene groups to provide branched or cross-linked polymers. U.S. Pat. No. 6,156,812 discloses polymers which contain both cyclopentadienone- and phenylacetylene-backbone groups.

In WO 00/31183, cross-linkable compositions comprising a cross-linkable hydrocarbon-containing matrix precursor and a separate pore forming substance (poragen) which are curable to form low dielectric constant insulating layers for semiconductor devices were disclosed. By partially curing the precursor to form a matrix containing occlusions of the poragen and then removing the pore generating material to form voids or pores in the matrix material, lower dielectric constant insulating films may be prepared.

It has now been discovered that the use of a curable matrix resin comprising only phenyethynyl functional groups and cyclopentadienone groups requires relatively high cure temperatures to achieve significant cross-link densities. Addition of a separate ethynyl functional monomer to increase the rate of cross-link formation results in a more complex multicomponent formulation and increased loss of monomer through evaporation. If a pore forming material is present in the formulation, poor initial matrix cross-link density can result in pore collapse, leading to variation in the electronic properties of the resulting film. This is particularly problematic when low temperature resistant pore forming materials, such as polyacrylate particles, are employed. Such materials decompose at lower processing temperatures leading to the need for monomers having improved low temperature cross-linking properties. Single component curable compositions meeting the foregoing requirements, especially those that are capable of providing homogeneous, porous matrices at reduced processing temperatures are particularly desired.

According to a first embodiment of the present invention there is provided a compound (monomer) comprising i) one or more arylethynyl groups (A-functional groups), ii) one or more ring structures comprising two conjugated carbon-to-carbon double bonds and a leaving group L (B-functional groups), and iii) one or more ethynyl groups (C'-functional groups), characterized in that said A- and C'-functional groups are capable of reaction under cycloaddition reaction conditions with said B-functional groups to thereby form a cross-linked, polyphenylene polymer.

According to a second embodiment of this invention, there is provided a curable oligomer or polymer made by at least a partial reaction of the C' and B groups of the foregoing monomer, a mixture thereof, or a composition comprising the same under cycloaddition reaction conditions. In this embodiment of the invention the curable oligomer or polymer comprises an initial polymerization or cross-linking by reaction of at least some B and C' groups, and optionally some A and B groups, and a remainder comprising at least some reactive A and B functional groups and optionally some C' groups remaining as pendant groups, terminal groups, or as groups within the backbone of the oligomer or polymer.

According to a third embodiment of the invention, C' groups on the monomer or on the curable oligomer or polymer of the second embodiment are reacted with one or more addition polymerizable monomers, telegens or graft polymerizable monomers or polymers, thereby incorporating bound poragen moieties into said monomer, oligomer or polymer.

According to a fourth embodiment of the invention, residual C' groups on the monomer or on the curable oligomer or polymer of the second or third embodiment are reacted with one another, optionally in the presence of one or more addition polymerizable monomers, telegens or graft polymerizable monomers, thereby forming a partially cross-linked matrix, optionally containing bound poragen moieties.

According to a fifth embodiment this invention is a crosslinked polymer made by curing and crosslinking the foregoing curable monomers or oligomers of the first through third embodiments, or polymers or compositions comprising the same. Desirably, if poragens are present in the monomers or oligomers, the resulting cross-linked polymer has improved low temperature cross-link density and an increased cross-link formation rate and the cured polymer possesses improved structural integrity.

According to a sixth embodiment of the invention there is provided a process for making a porous, solid article comprising a vitrified polyarylene polymer which process comprises providing the foregoing curable monomers or oligomers of the first through third embodiments, or polymers or compositions comprising the same; partially polymerizing the monomer under cycloaddition reaction conditions optionally in the presence of a solvent, optionally one or more addition polymerizable monomers, telegens or graft polymerizable monomers, and/or one or more separately added poragens, thereby forming a curable oligomer or polymer containing composition; and crosslinking the composition to form a solid polyarylene polymer optionally containing bound poragens or separately added poragens. In a further step, the optional solvent, bound poragens, and/or separately added poragens may be removed.

According to a seventh embodiment, this invention is an article made by the above method, desirably a porous article formed by removal of bound poragens and/or separately added poragens. Desirably, said article contains a homogeneous distribution of pores and improved structural integrity.

According to an eighth embodiment of the invention, the foregoing article is a film and the construct is a semiconductor device, such as an integrated circuit, incorporating the film as an insulator between circuit lines or layers of circuit lines therein.

The monomers are highly soluble in typical solvents used in fabrication of semiconductor devices, and may be employed in formulations that are coated onto substrates and vitrified to form films and other articles. The compositions including a bound poragen are desirable in order to obtain films having uniformly distributed small pores having a reduced potential for pore collapse or coalescence during the chip manufacturing process, uniform electrical properties, and low dielectric constants.

For purposes of United States patent practice, the contents of any patent, patent application or publication referenced herein is hereby incorporated by reference in its entirety herein, especially with respect to its disclosure of monomer, oligomer or polymer structures, synthetic techniques and general knowledge in the art. If appearing herein, the term "comprising" and derivatives thereof is not intended to exclude the presence of any additional component, step or procedure, whether or not the same is disclosed herein. In order to avoid any doubt, all compositions claimed herein through use of the term "comprising" may include any additional additive, adjuvant, or compound, unless stated to the contrary. In contrast, the term, "consisting essentially of" if appearing herein, excludes from the scope of any succeeding recitation any other component, step or procedure, excepting those that are not essential to operability. The term "consisting of", if used, excludes any component, step or procedure not specifically delineated or listed. The term "or", unless apparent from the context or stated otherwise, refers to the listed members individually as well as in any combination.

As used herein the term "aromatic" refers to a polyatomic, cyclic, ring system containing $(4\delta+2)$ π-electrons, wherein $\delta$ is an integer greater than or equal to 1. The term "fused" as used herein with respect to a ring system containing two or more polyatomic, cyclic rings means that with respect to at least two rings thereof, at least one pair of adjacent atoms is included in both rings.

"A-functionality" refers to a single arylethynyl group.

"B-functionality" refers to the ring structure comprising two conjugated carbon-to-carbon double bonds and a leaving group L.

"b-staged" refers to the oligomeric mixture or low molecular weight polymeric mixture resulting from partial polymerization of a monomer or monomer mixture. Unreacted monomer may be included in the mixture.

"C'-functionality" refers to ethynyl functional groups.

"Cross-linkable" refers to a matrix precursor that is capable of being irreversibly cured, to a material that cannot be reshaped or reformed. Cross-linking may be assisted by thermal, UV, microwave, x-ray, or e-beam irradiation.

"Dienophile" refers to a group that is able to react with the conjugated, double bonded carbon groups according to the present invention, preferably in a cycloaddition reaction involving elimination of the L group and aromatic ring formation.

"Inert substituent" means a substituent group which does not interfere with any subsequent desirable polymerization reaction of the monomer or b-staged oligomer and does not include further polymerizable moieties as disclosed herein.

"Matrix precursor" means a monomer, prepolymer, polymer, or mixture thereof which upon curing or further curing, forms a cross-linked polymeric material.

"Monomer" refers to a polymerizable compound or mixture thereof.

"Matrix" refers to a continuous phase surrounding dispersed regions of a distinct composition or void.

"Poragen" refers to polymeric or oligomeric components that may be combined with the monomers, oligomers or polymers of the invention, and which may be removed from the initially formed oligomer or, more preferably, from the vitrified (that is the fully cured or cross-linked) polymer matrix, resulting in the formation of voids or pores in the polymer. Poragens may be removed from the matrix polymer by any suitable technique, including dissolving with solvents or, more preferably, by thermal decomposition. A "bound poragen" refers to a poragen that is chemically bound or grafted to the monomer, oligomer, or vitrified polymer matrix through reaction with an A or C'-functional group.

The Monomers and Their Syntheses

The monomers of the present invention preferably comprise one or more than one arylethynyl groups (A-functional groups); one or more hydrocarbon- or heteroatom substituted hydrocarbon-rings having two conjugated carbon to carbon double bonds and the leaving group, L (B-functional groups); one or more ethynyl groups (C'-functional groups); and, optionally, inert substituents or components.

Preferred B-functional groups comprise cyclic, five-membered, conjugated diene rings where L is —O—, —S—, —C(O)—, or —(SO$_2$)—, or a six membered, conjugated diene ring where L is —N═N—, or —OC(O)—. Optionally, two of the carbon atoms of the ring structure and their substituent groups taken together may also form an aromatic ring, that is, the 5 or 6 membered ring structures may be part of a fused, multiple aromatic ring system.

Most preferably, L is —C(O)— such that the ring is a cyclopentadienone group or benzcyclopentadienone group. Examples of such most preferred cyclopentadienone rings are those containing aryl groups at the 2, 3, 4, or 5 positions thereof, more preferably at the 2, 3, 4 and 5 positions thereof.

Suitable arylethynyl groups (A-functionality) for use herein correspond to the formula: —C≡CR$^1$, wherein R$^1$ is C$_{6-20}$ aryl, preferably phenyl, naphthyl, biphenyl or p-phenoxyphenyl; most preferably phenyl.

Ethynyl groups (C'-functionality) for use herein correspond to the formula: —C≡CR$^2$, wherein R$^2$ is hydrogen, C$_{1-6}$ alkyl, C$_{1-6}$ hydroxyalkyl, or trimethylsilyl; preferably hydrogen.

The monomers of the present invention may be depicted generically by the formula: AxByC'z, wherein A, B and C' stand for A-functionality, B-functionality and C'-functionality respectively, and x, y and z are integers greater than or equal to one.

Examples of suitable monomers according to the invention are compounds corresponding to the formula,

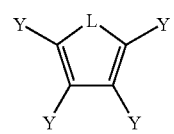

wherein L is —O—, —S—, —N═N—, —C(O)—, —(SO$_2$)—, or —OC(O)—;

Y is independently in each occurrence hydrogen, halogen, an unsubstituted or inertly substituted hydrocarbyl group, especially an aryl group, more especially a phenyl group, Y', or two adjacent Y groups together with the carbons to which they are attached form a fused aromatic ring, Y' is a single covalent bond or a divalent derivative of an unsubstituted or inertly substituted hydrocarbyl group joining two or more divalent remnants of the foregoing structure, and in at least one occurrence, Y is —Y'''(—C≡CR$^1$)$_m$, and in at least one other occurrence, Y is —Y''—(C≡CR$^2$)$_n$;

or in at least one occurrence, Y is —Y''(—C≡CR$^1$)$_m$(C≡CR$^2$)$_n$; wherein,

Y'' is a single covalent bond or a polyvalent derivative of an unsubstituted or inertly substituted hydrocarbyl group, preferably an aromatic hydrocarbyl group;

R$^1$ is C$_{6-20}$ aryl, preferably phenyl, naphthyl, biphenyl or p-phenoxyphenyl;

R$^2$ is hydrogen, C$_{1-4}$ alkyl, C$_{1-6}$ hydroxyalkyl, or trimethylsilyl, preferably hydrogen; and m and n are integers from 1 to 5.

Preferred monomers according to the present invention are 3-substituted cyclopentadienone compounds or 3,4-disubstituted cyclopentadienone compounds, represented by the formula:

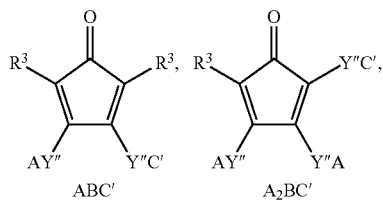

ABC'  A$_2$BC'

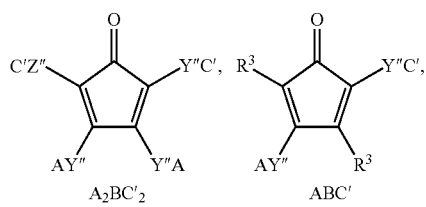

A$_2$BC'$_2$  ABC'

1p;2p

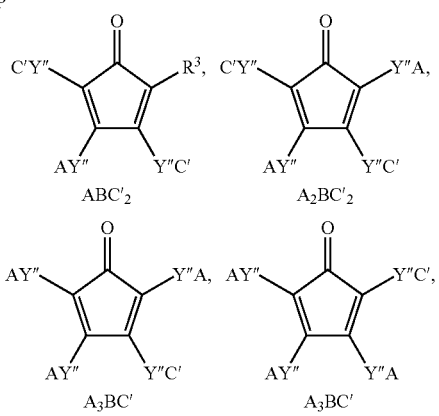

ABC'$_2$  A$_2$BC'$_2$

A$_3$BC'  A$_3$BC'

-continued

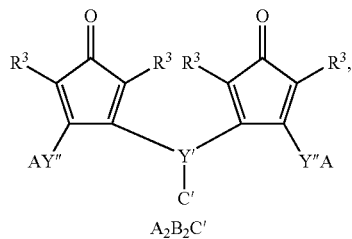

A$_2$B$_2$C'

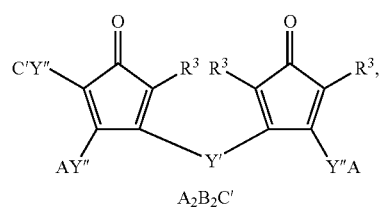

A$_2$B$_2$C'

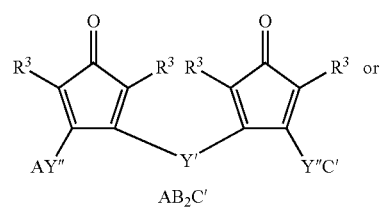

AB$_2$C'

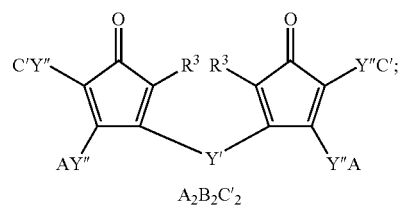

A$_2$B$_2$C'$_2$ wherein R$^3$ is C$_{6-20}$ aryl or inertly substituted aryl, more preferably, phenyl, biphenyl, p-phenoxyphenyl or naphthyl, and A, C', Y' and Y'' are as previously defined.

Highly preferred monomers according to the present invention are those wherein A is phenylethynyl and C' is a ethynyl. Examples include compounds of the following formulas:

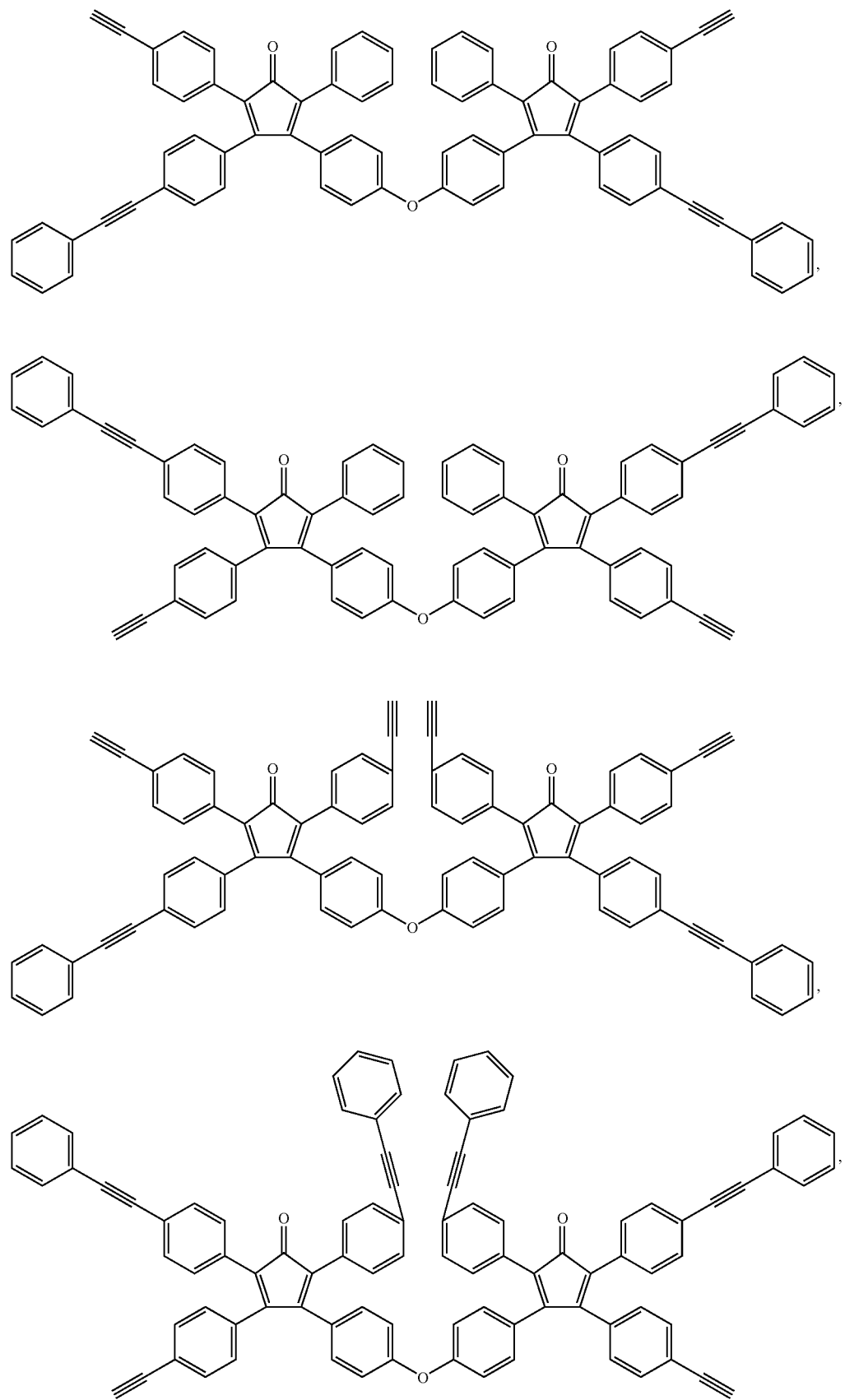

-continued
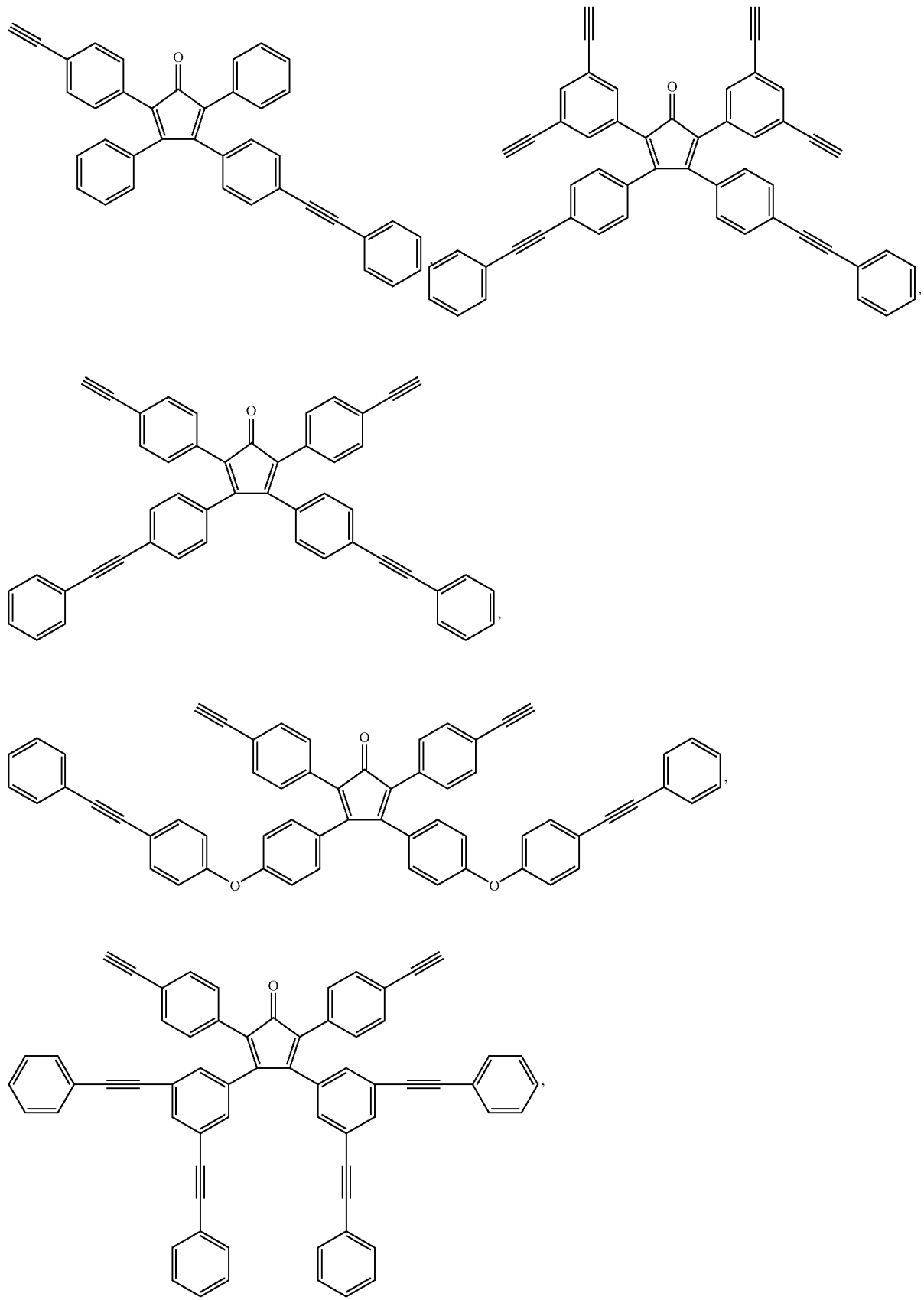

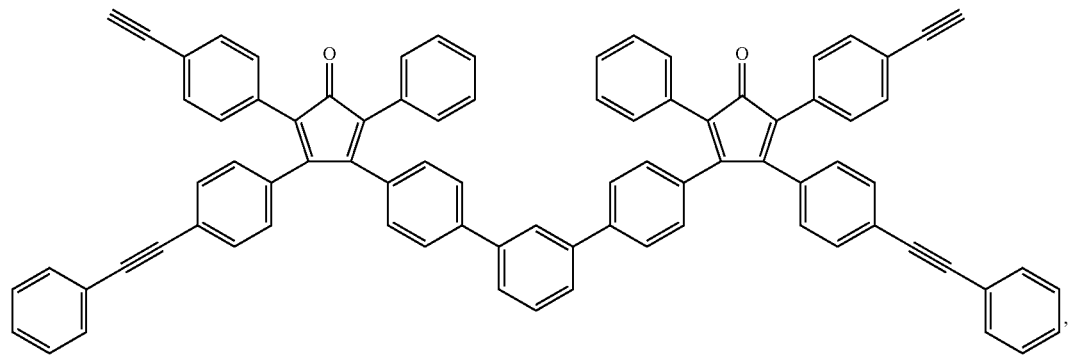
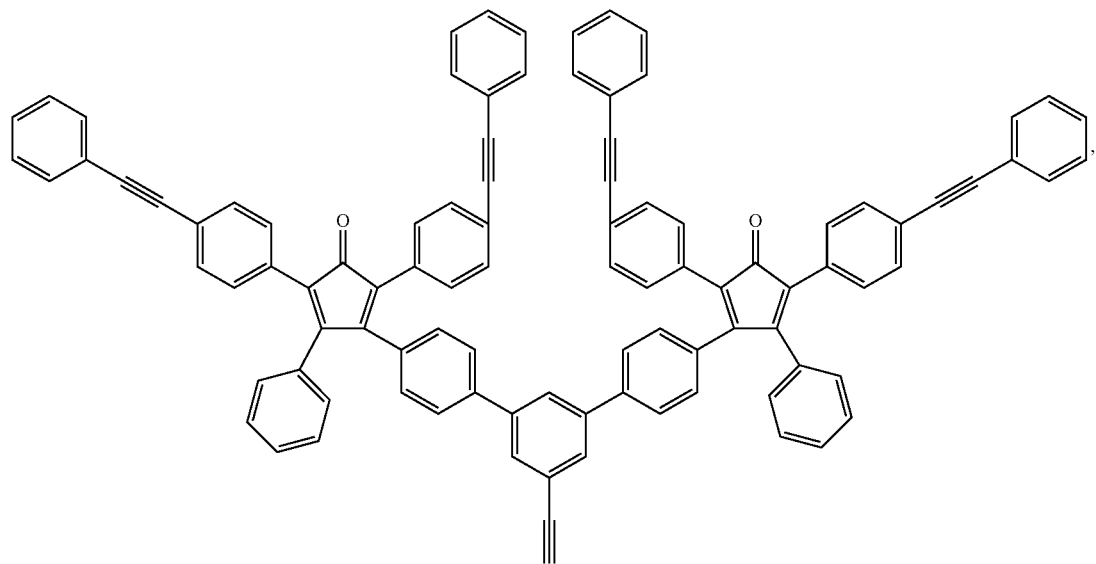
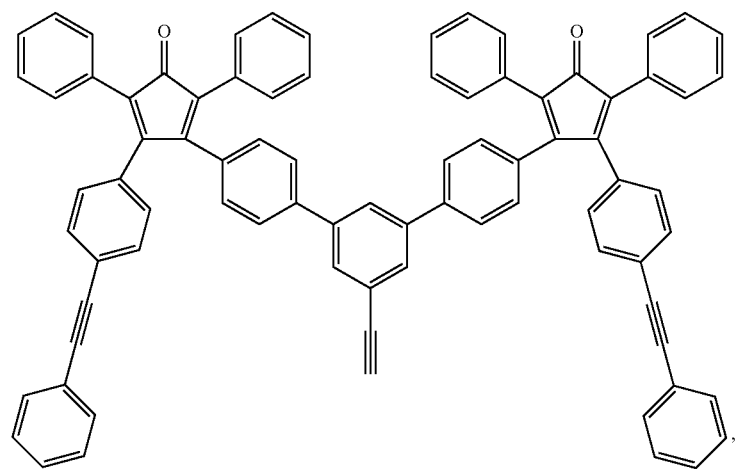

-continued

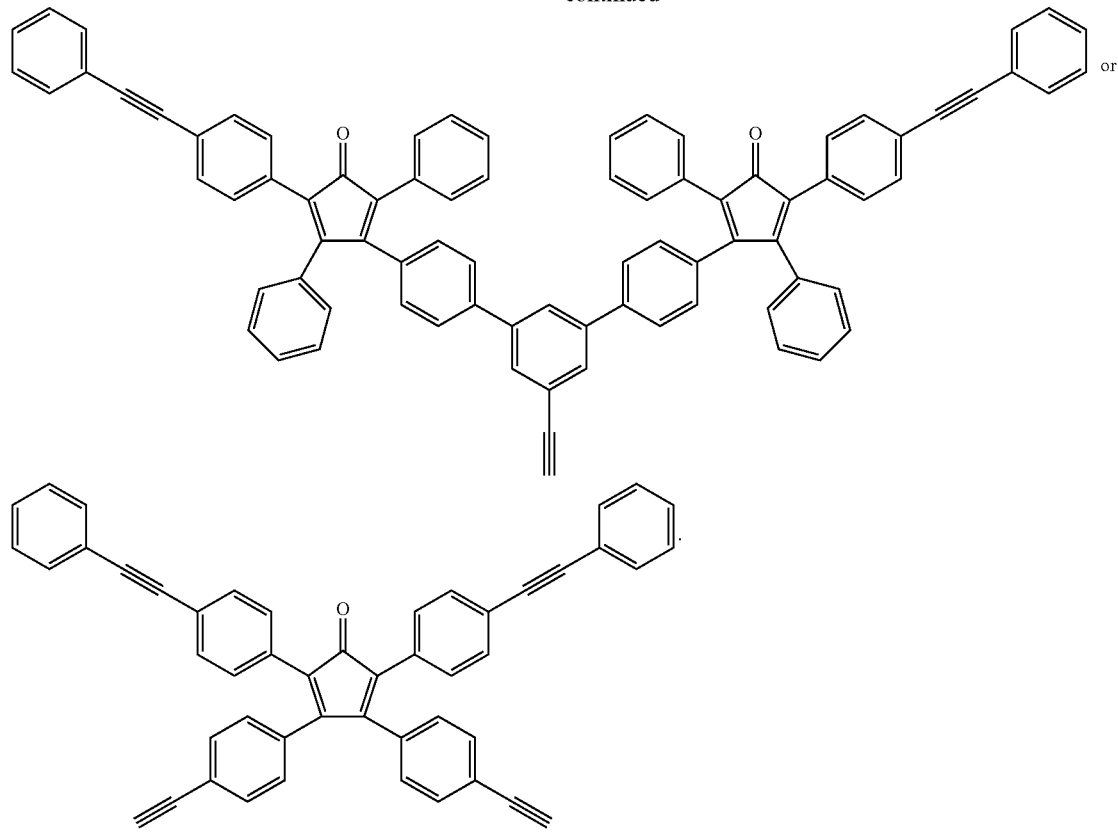

Synthesis of AxByC'z Monomers

The monomers according to the present invention may be made by the condensation of diaryl-substituted acetone compounds with aromatic polyketones using conventional methods. Exemplary methods are disclosed in *Macromolecules.* 28, 124-130 (1995); *J. Org. Chem.,* 30, 3354 (1965); *J. Org. Chem.,* 28, 2725 (1963); *Macromolecules.* 34, 187 (2001); *Macromolecules* 12, 369 (1979); *J. Am. Chem. Soc.* 119, 7291 (1997); and U.S. Pat. No. 4,400,540.

More preferably, the monomers may be made by the condensation of the following synthons, or molecular components, wherein R and R' are either H, phenylethynyl, or ethynyl.

-continued

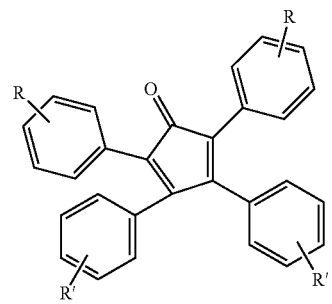

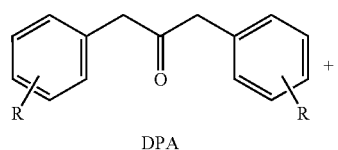
DPA

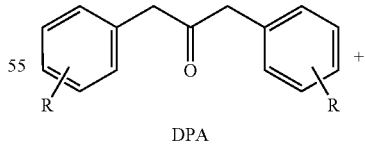
DPA

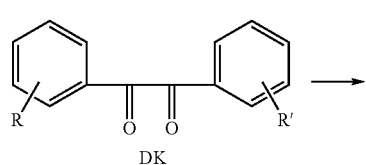
DK

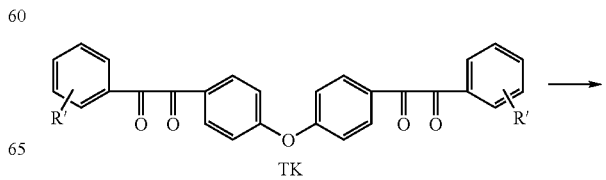
TK

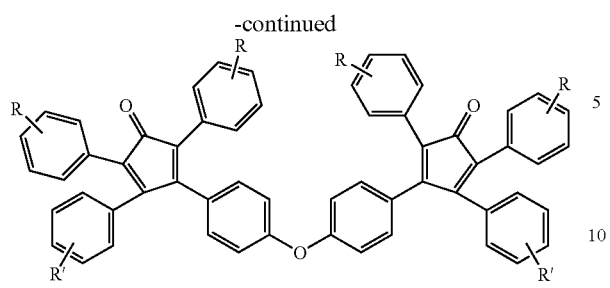
Example of diphenylacetone or DPA synthones are represented by following formulas:
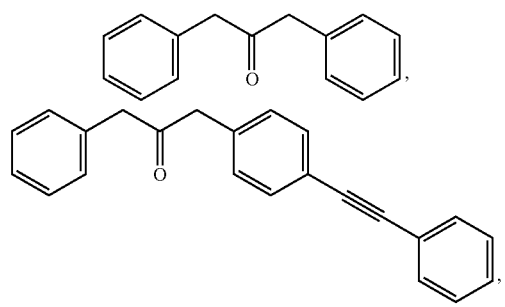
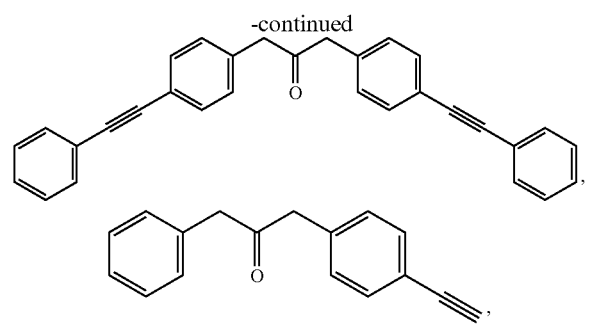
Example of diketone (DK) or tetraketone or (TK) synthons are represented by following formulas, where C' groups are as previously defined:
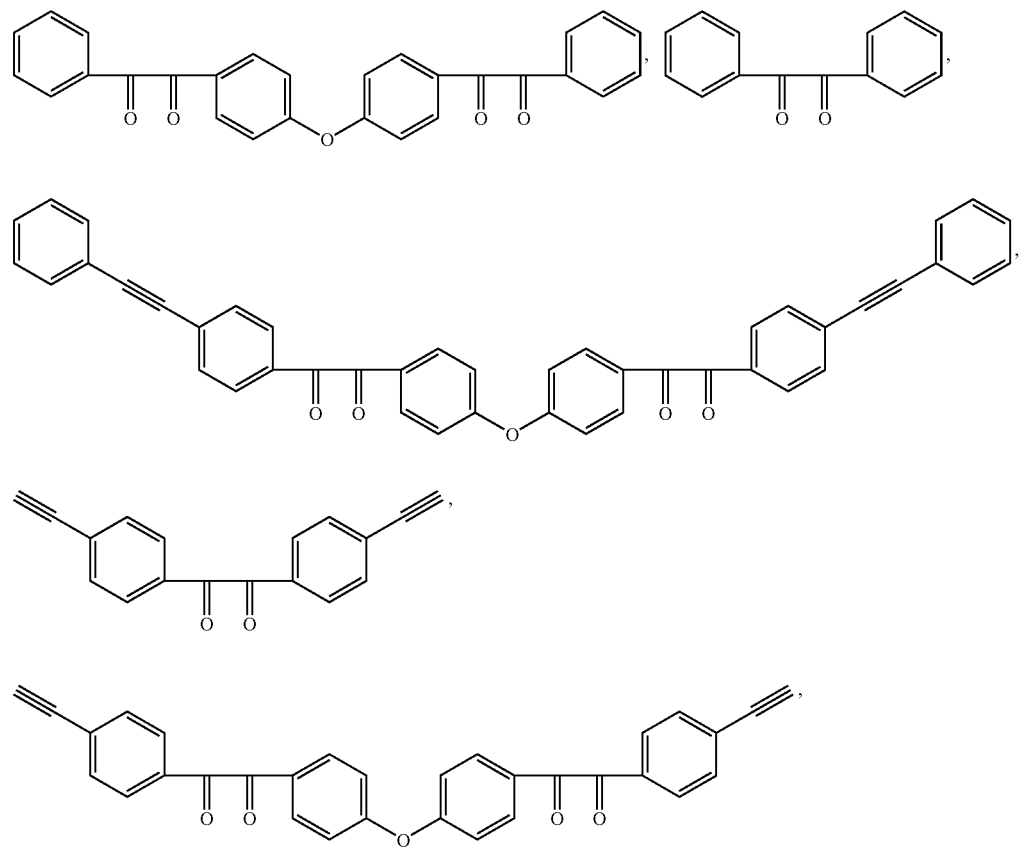

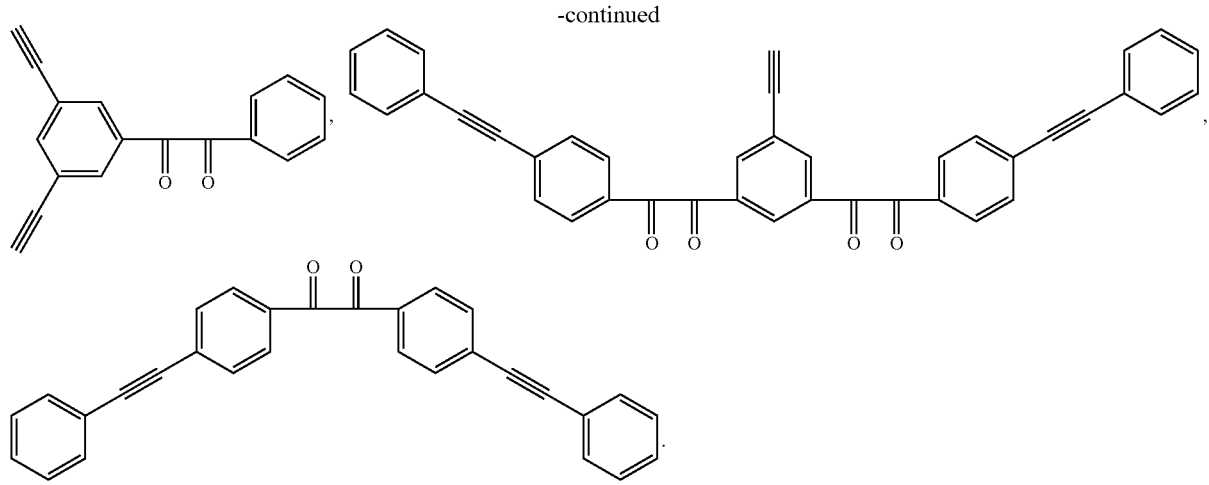

Various DK, TK and DPA synthons can be prepared, using methods known in the art, as intermediates to produce any desired AxByC'z monomer, preferably $A_2B_2C'$ monomers. Briefly, said methods comprise: (a) Friedel-Crafts acylation of aromatic compounds such as diphenylether with 4-bromophenylacetylchloride, 3,5-dibromophenylacetyl chloride or phenylacetyl chloride, (b) modified Kornblum oxidation of the acylation product using dimethylsulfoxide and hydrobromic acid, (c) a modified Heck reaction with 2-methyl-3-butyn-2-ol followed by treatment with base or reaction with (trimethylsilyl)acetylene followed by treatment with potassium carbonate to generate ethynyl groups, and (d) (phenylethynylation) of the bromophenyl mono-, di- or tetraketones with phenylacetylene using palladium catalysts, a tertiary amine, and a solvent which is essentially inert to both reactants and products. The final step is bis(cyclopentadienone) formation via Aldol condensation of ketone with acetone functionality using a quaternary ammonium hydroxide catalyst and one or more solvents that are essentially inert to both reactants and products. If desired, the generation of ethynyl functionality by base treatment as disclosed in step (c) can be delayed to a later stage of the synthesis in order to prevent competitive reaction of ethynyl groups.

b-Staging of AxByC'z Monomer

Preparation of Oligomers and Partially Cross-Linked Polymers (b-Staging) can be accomplished by heating a mixture comprising the foregoing monomer or mixture of monomers, optionally one or more additional, polymerizable monomers, including graftable bound poragen precursors, an optional solvent or diluent, and an optional separately added poragen.

While not desiring to be bound by their belief, it is believed that polyphenylene oligomers and polymers are formed through a Diels-Alder reaction of the B-functional groups (preferably cyclopentadienone groups) with the A- and/or C'-functional groups (preferably phenylacetylene and acetylene groups respectively). Desirably the ethynyl functionality reacts preferentially with the B-functional groups and at a lower reaction temperature than the phenylethynyl groups. The b-staged product desirably contains quantities of cyclopentadienone and phenylethynyl end groups, and optionally ethynyl groups. Upon further heating of the mixture or an article coated therewith, additional crosslinking can occur through the Diels-Alder reaction of the remaining cyclopentadienone or B groups with the remaining phenylethynyl or A groups and/or C' groups. Ideally, cyclopentadienone and phenylacetylene groups are consumed at the same rate under Diels-Alder reaction conditions, preferably at temperatures from 280 to 350° C., more preferably from 285 to 320° C. The temperature is desirably selected such that minimal or no reaction between two A groups or two B groups occurs. However, in one embodiment, improved polymer properties are obtainable by the reaction of at least some C' functional groups with B-functional groups, prior to or concomitant with reaction between A and B groups.

The cross-linking reaction is preferably halted prior to the reaction of significant quantities of A, B, and/or C' functionality to avoid gel formation. The oligomer may then be applied to a suitable surface prior to further advancement or curing of the composition. While in an oligomerized or b-stage, the composition is readily applied to substrates by standard application techniques, and forms a level surface coating which covers (planarizes) components, objects or patterns on the surface of the substrate. Preferably, at least ten percent of the monomer remains unreacted when b-staged. Most preferably, at least twenty percent of the monomer remains unreacted. One may determine the percentage of unreacted monomer by visible spectra analysis or SEC analysis.

Suitable solvents for preparing coating compositions of b-staged compositions include mesitylene, methyl benzoate, ethyl benzoate, dibenzylether, diglyme, triglyme, diethylene glycol ether, diethylene glycol methyl ether, dipropylene glyco methyl ether, dipropylene glycol dimethyl ether, propylene glycol methyl ether, dipropylene glycol monomethyl ether acetate, propylene carbonate, diphenyl ether, butyrolactone. The preferred solvents are mesitylene, gamma-butyrolactone, diphenyl ether and mixtures thereof.

Alternatively, the monomers can be polymerized in one or more solvents at elevated temperature and the resulting solution of oligomers can be cooled and formulated with one or more additional solvents to aid in processing. In another approach, the monomer can be polymerized in one or more solvents at elevated temperature to form oligomers or oligomer fractions, which can be isolated by precipitation into a non solvent. These isolated oligomers or oligomer fractions can then be redissolved in a suitable solvent for processing.

The monomers of the present invention or b-staged oligomers thereof are suitably, employed in a curable composition alone or as a mixture with other monomers containing two or more functional groups (or b-staged oligomers thereof) able to polymerize by means of a Diels-Alder or similar cycloaddition reaction. Examples of such other monomers include compounds having two or more cyclopentadienone functional groups and/or acetylene functional groups or mixtures thereof, such as those previously disclosed in U.S. Pat. Nos. 5,965,679 and 6,359,091. In the b-stage curing reaction, a dienophilic group reacts with the cyclic diene functionality, causing elimination of L and aromatic ring formation. Subsequent curing or vitrification may involve a similar cycloaddition or an addition reaction involving only the dienophilic functional groups.

Additional polymerizable monomers containing A, B and/or C' functionality may be included in a curable composition according to the present invention. Examples include compounds of the formula:

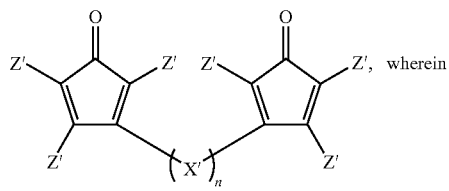 (I)

wherein

Z' is independently in each occurrence hydrogen, an unsubstituted or inertly substituted aromatic group, an unsubstituted or inertly substituted alkyl group, or —W—(C≡C—Q)$_q$;

X' is an unsubstituted or inertly substituted aromatic group, —W—C≡C—W—, or

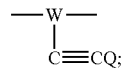

W is an unsubstituted or inertly substituted aromatic group, and

Q is hydrogen, an unsubstituted or inertly substituted $C_{6-20}$ aryl group, or an unsubstituted or inertly substituted $C_{1-20}$ alkyl group, provided that at least two of the X' and/or Z' groups comprise an arylethynyl group, q is an integer from 1 to 3; and n is an integer of from 1 to 10.

Examples of the foregoing polyfunctional monomers that may be used in conjunction with the monomers of the present invention include compounds of formulas II-XXV:

Formula II:

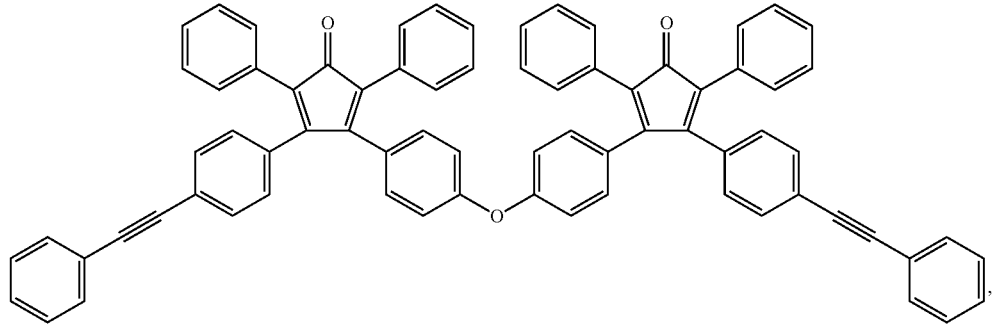

Formula III (a mixture of):

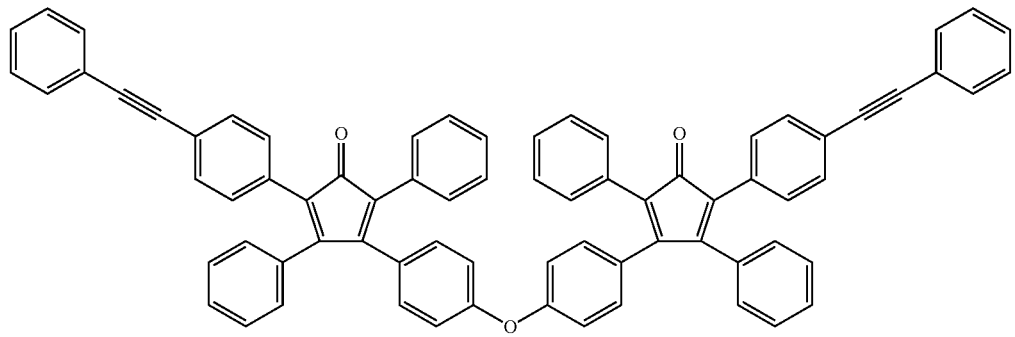

-continued
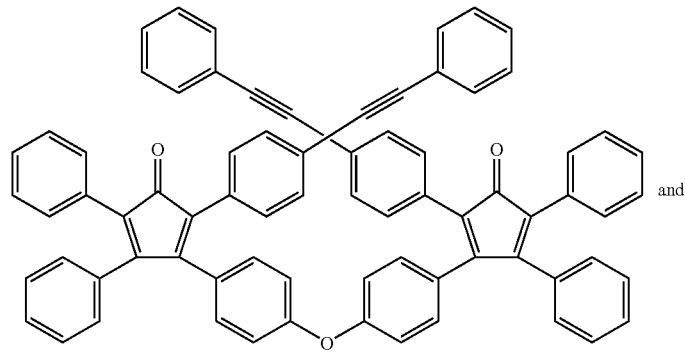 and
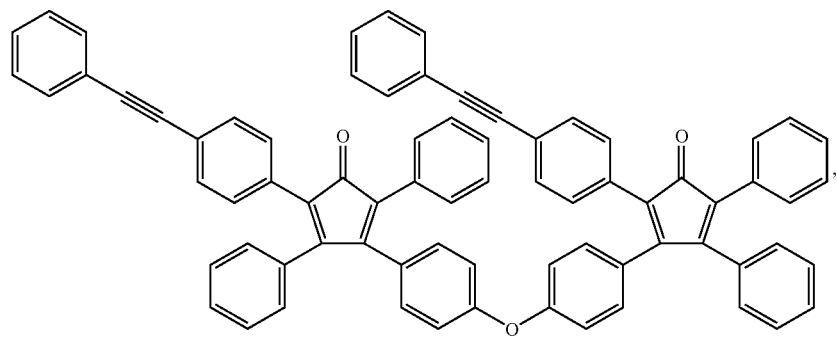,
Formula IV:
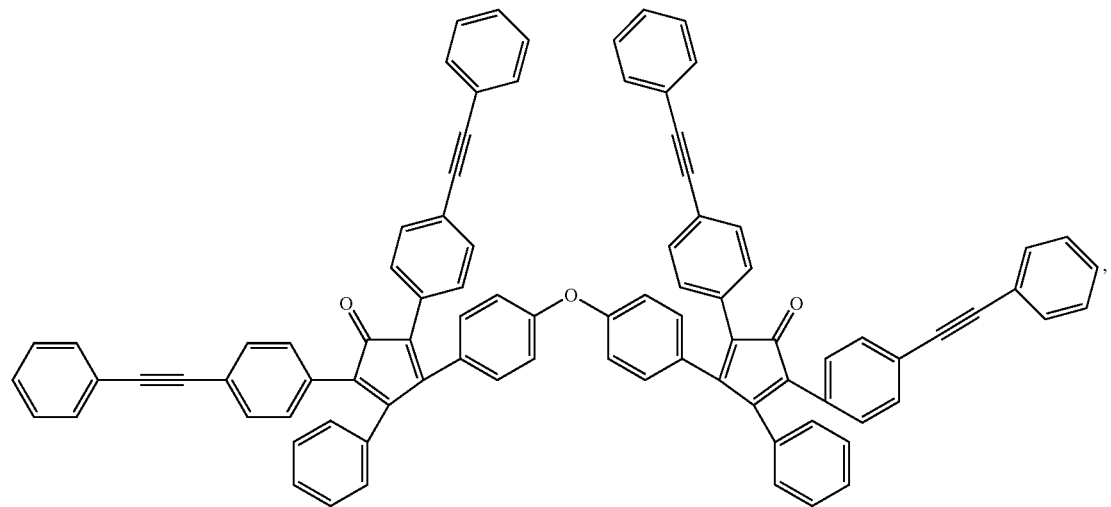,

-continued
Formula V:
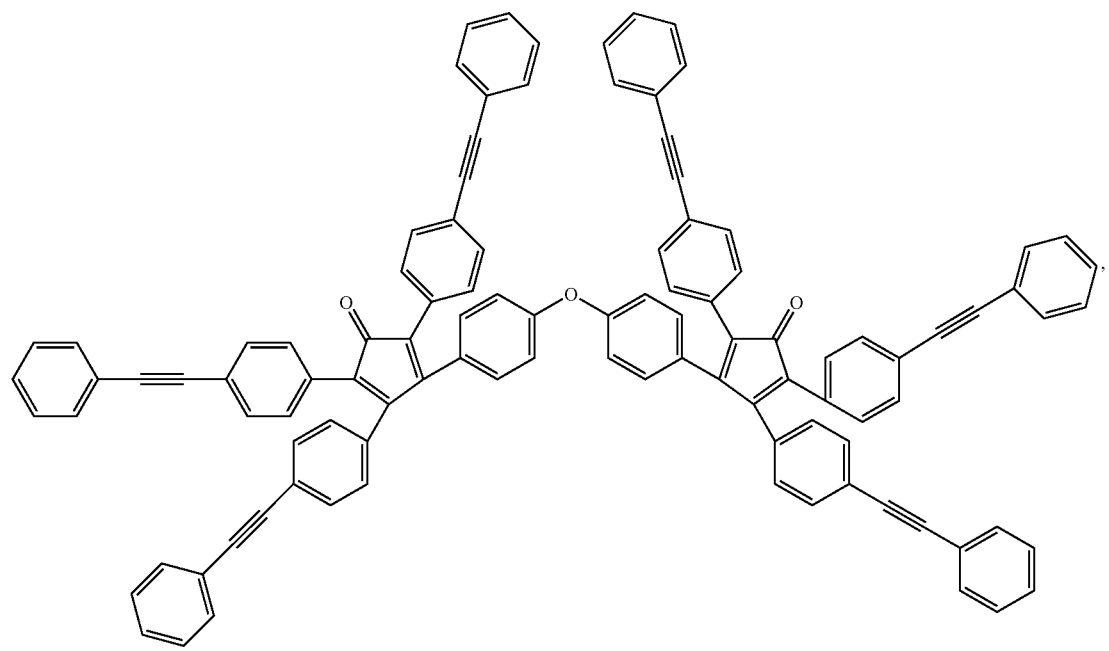
Formula VI:
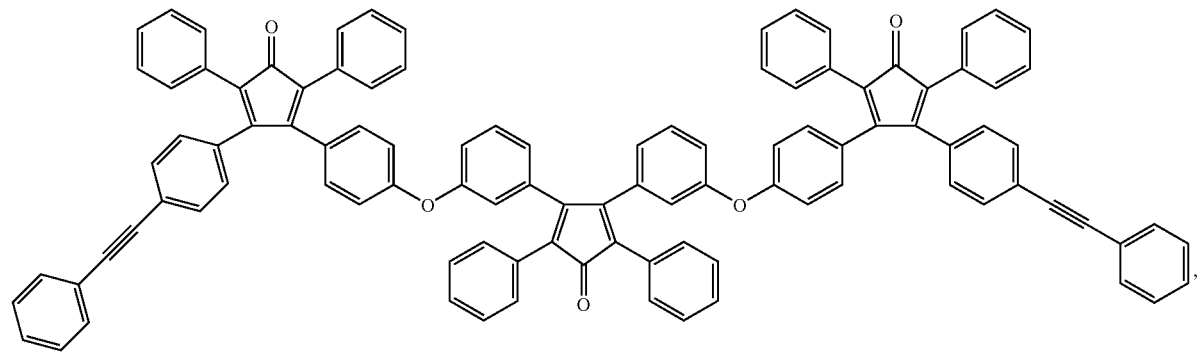
Formula VII:
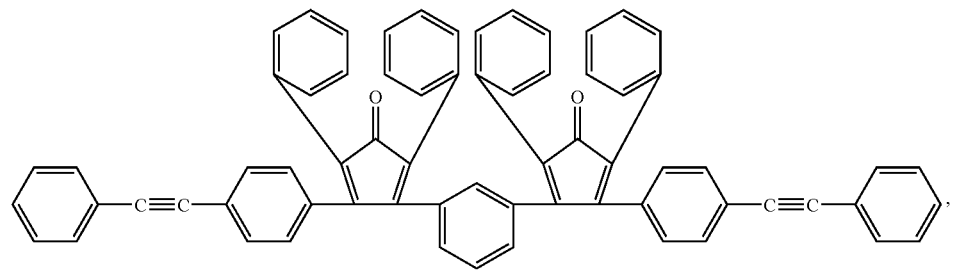
Formula VIII:
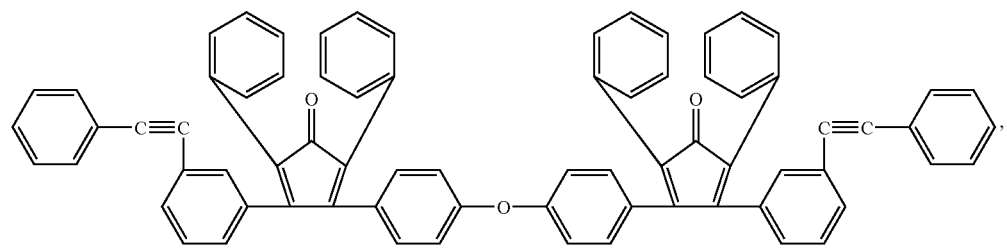

-continued
Formula IX:
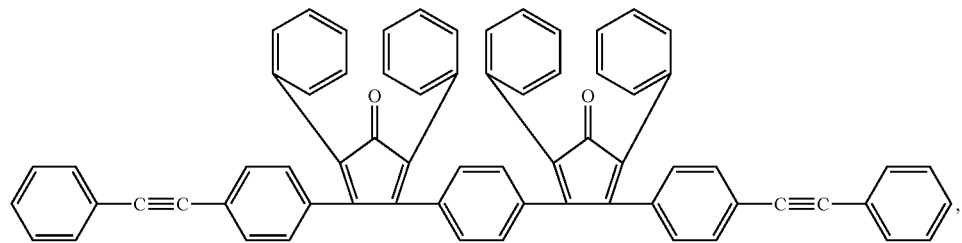
Formula X:
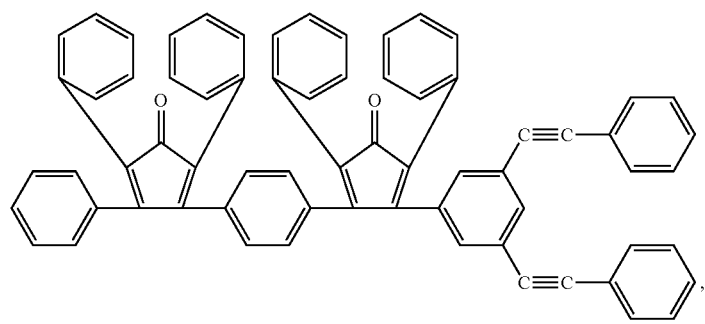
Formula XI:
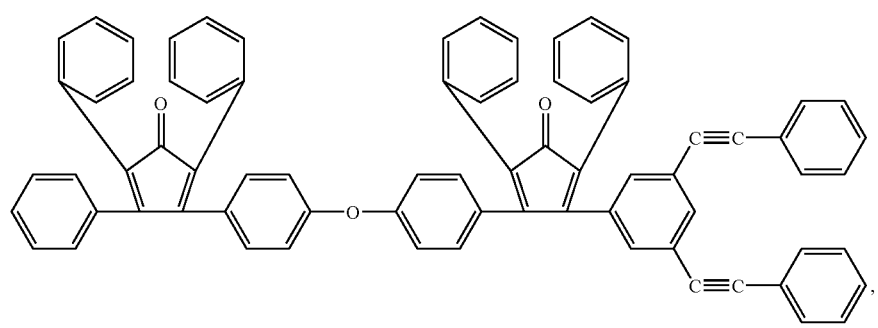
Formula XII:
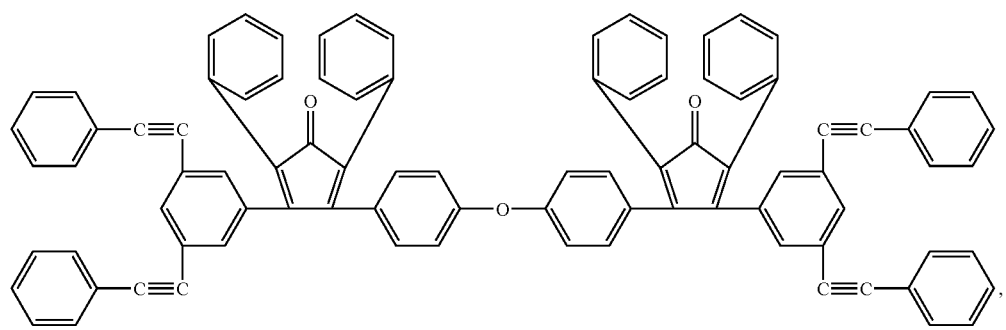
Formula XIII:
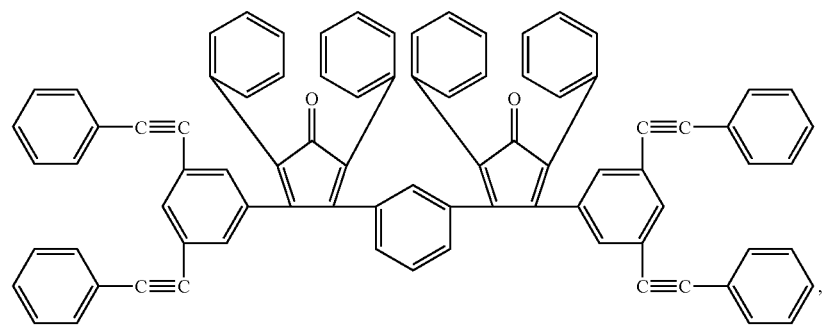

-continued
Formula XIV:
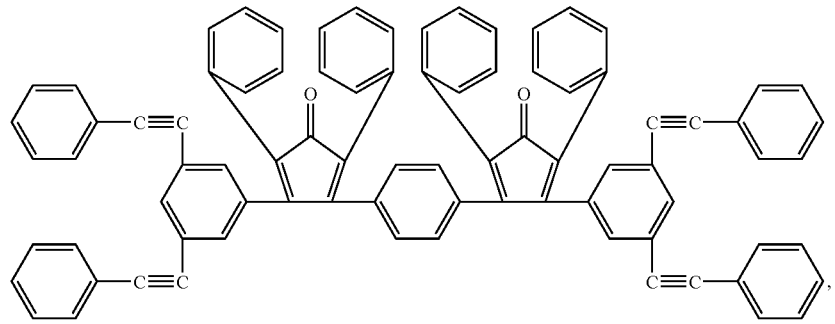
Formula XV:
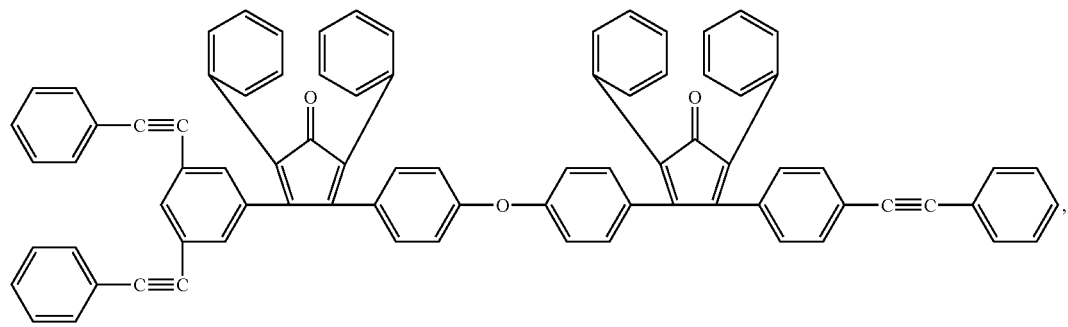
Formula XVI:
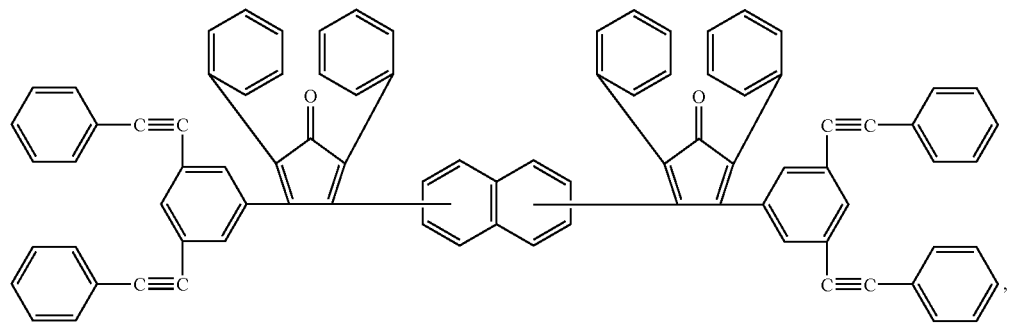
Formula XVII:
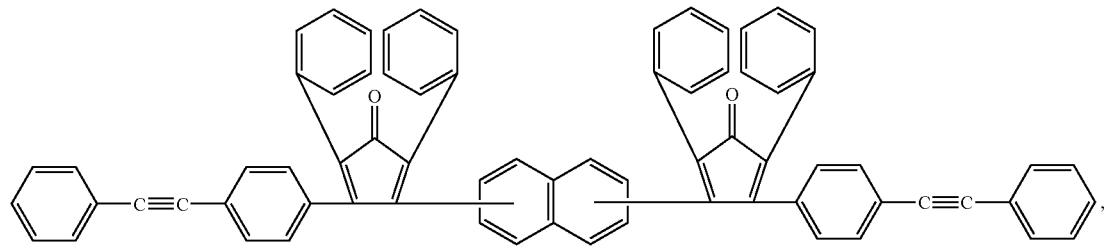
Formula XVIII:
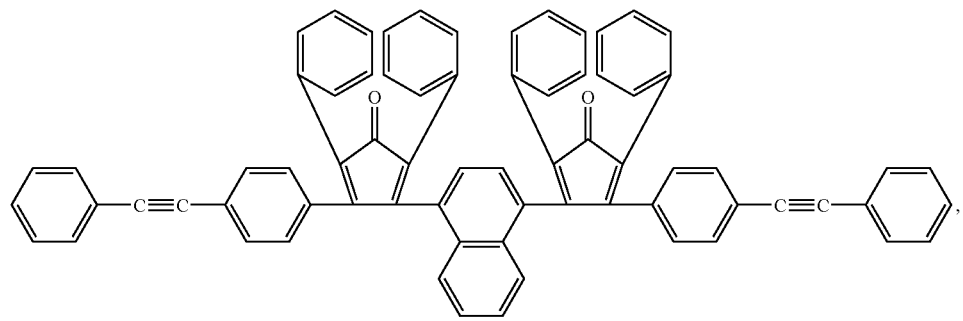

-continued
Formula XIX:
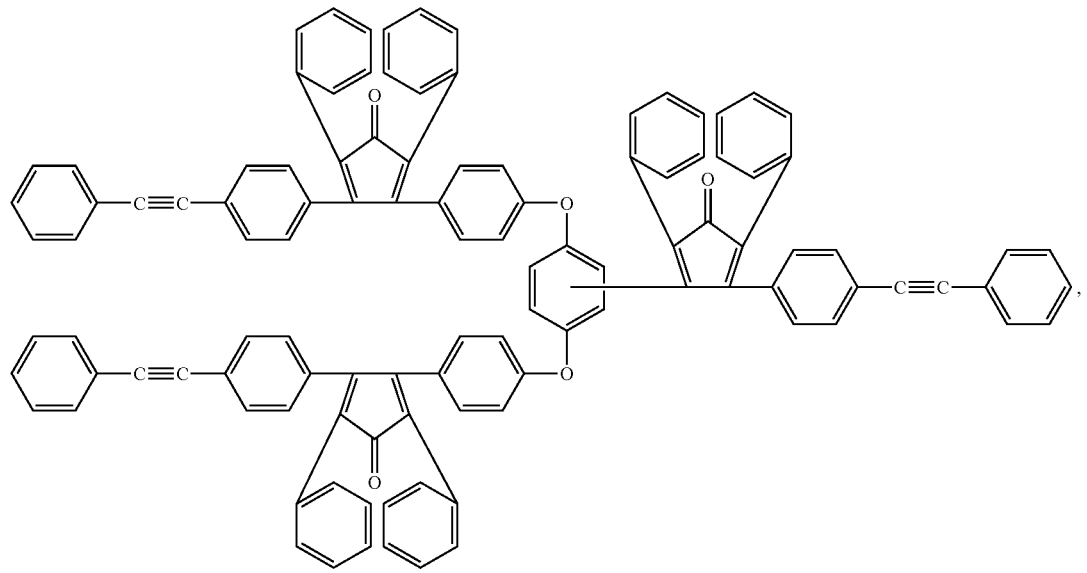
Formula XX (a mixture of):
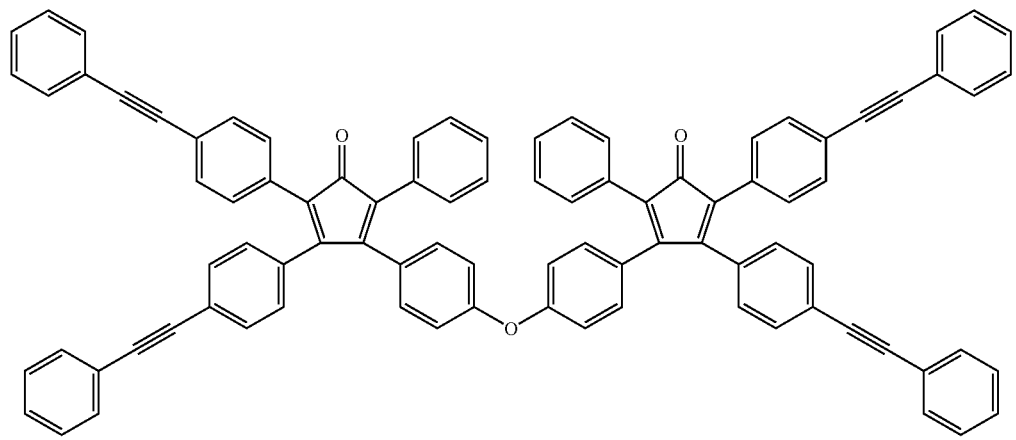
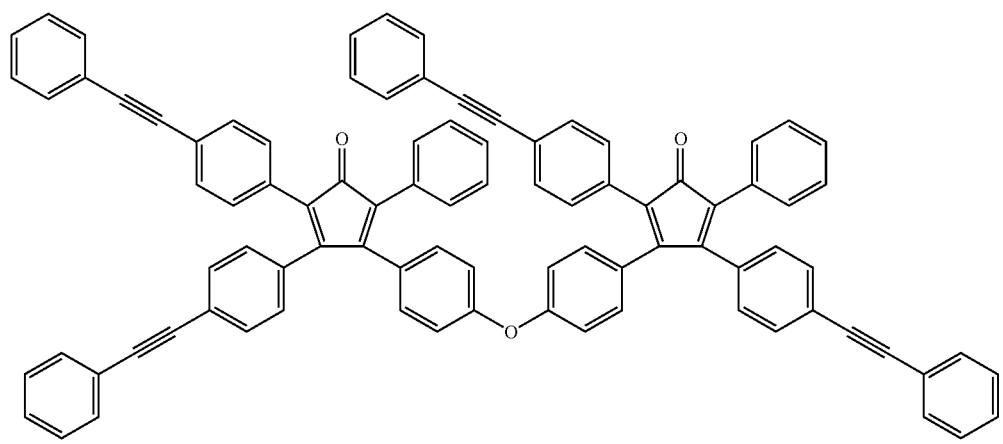

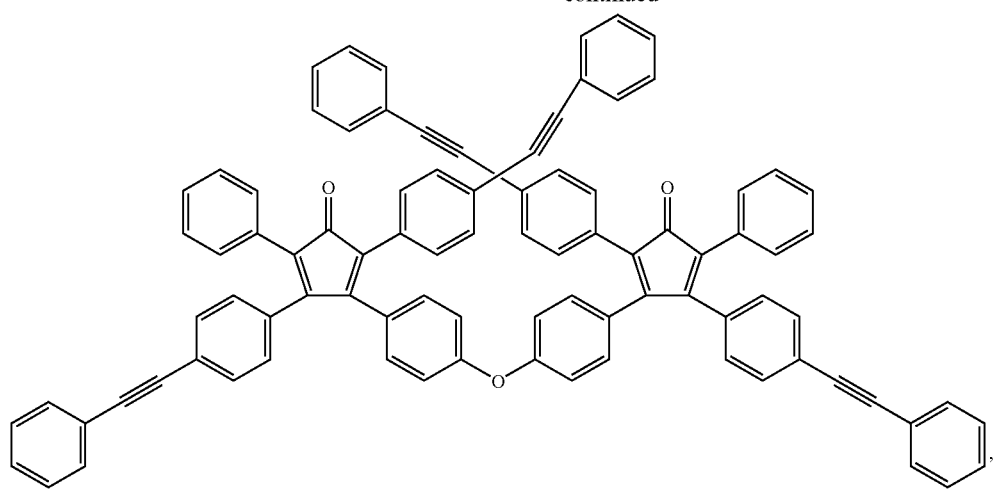
Formula XXI (a mixture of):
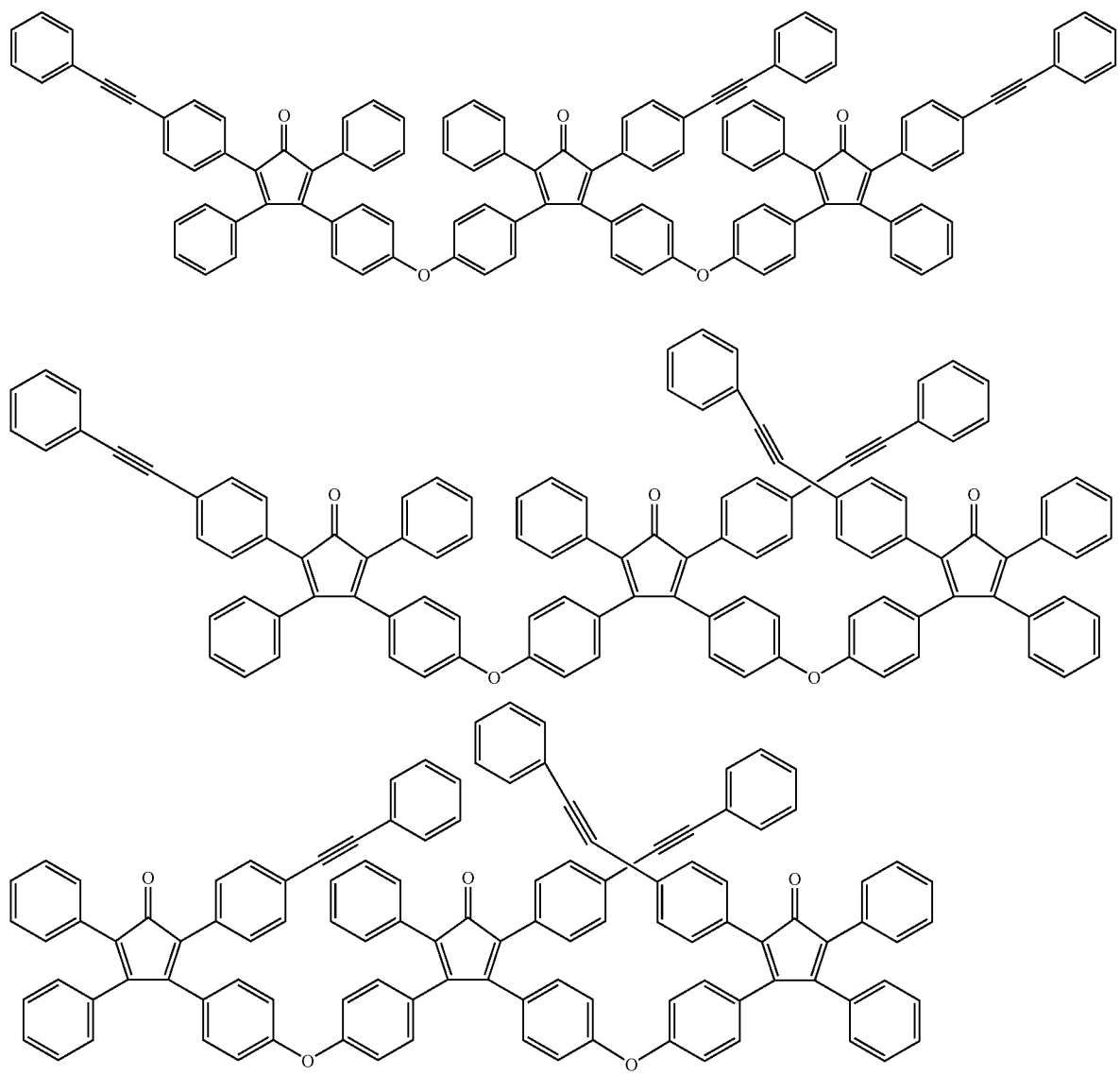

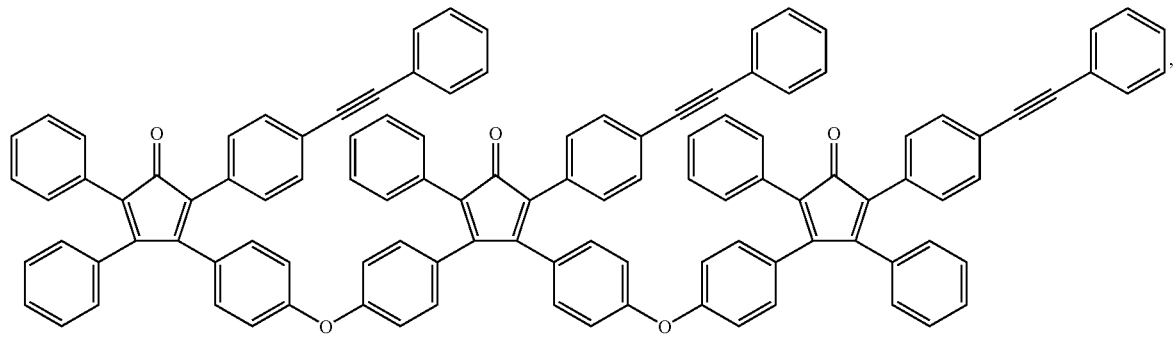
Formula XXII (a mixture of):
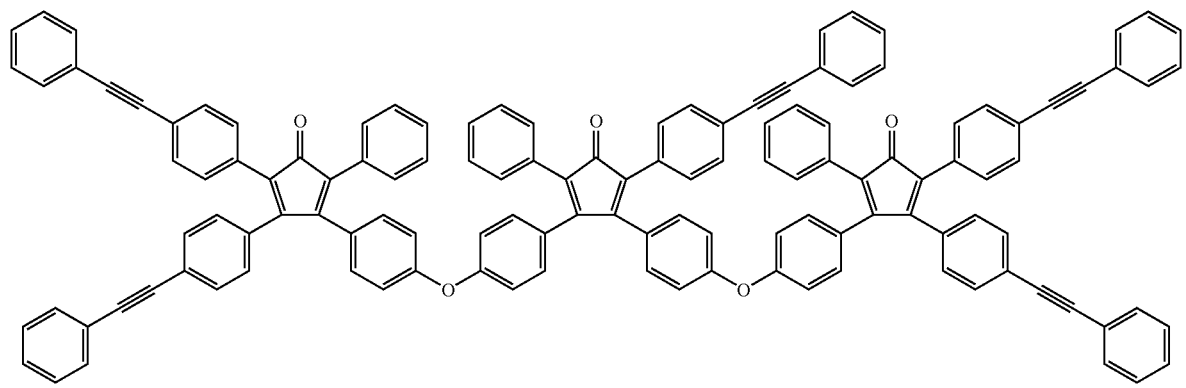
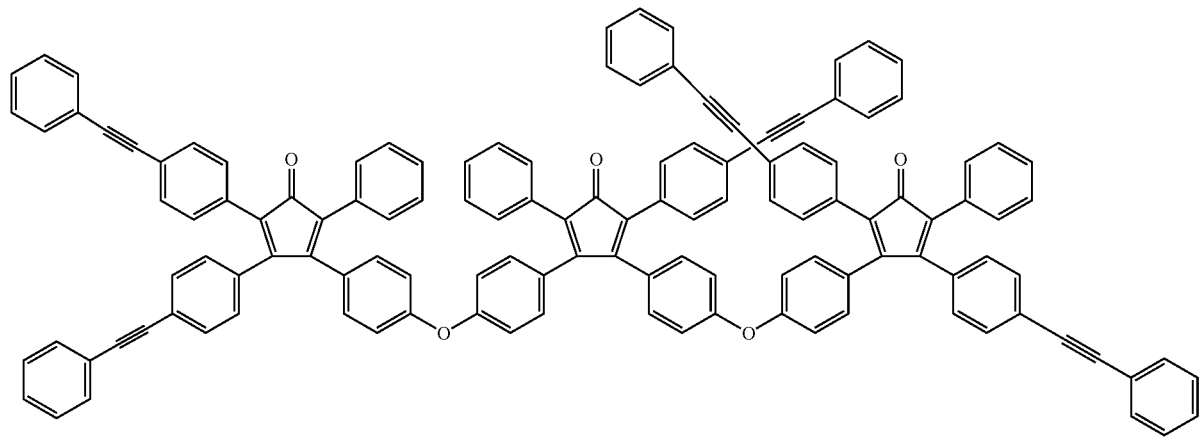
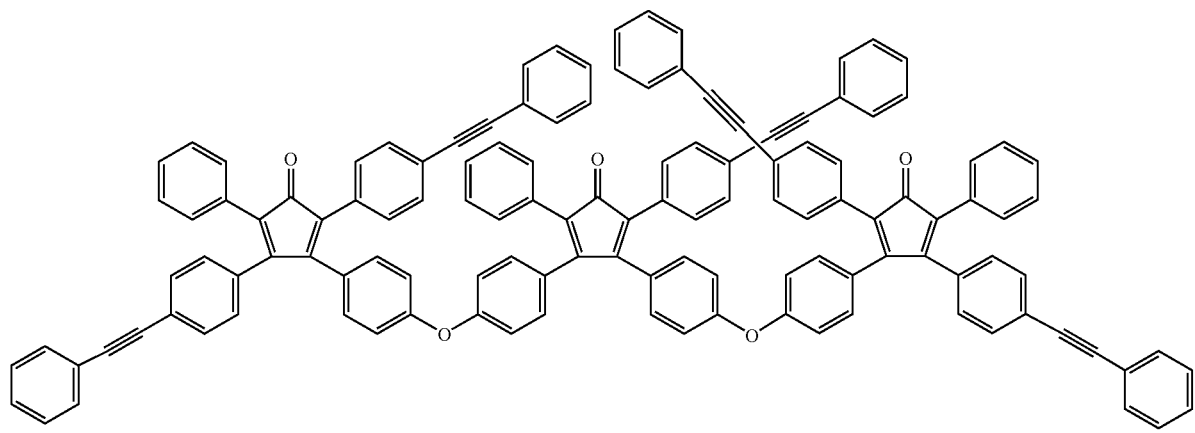

-continued
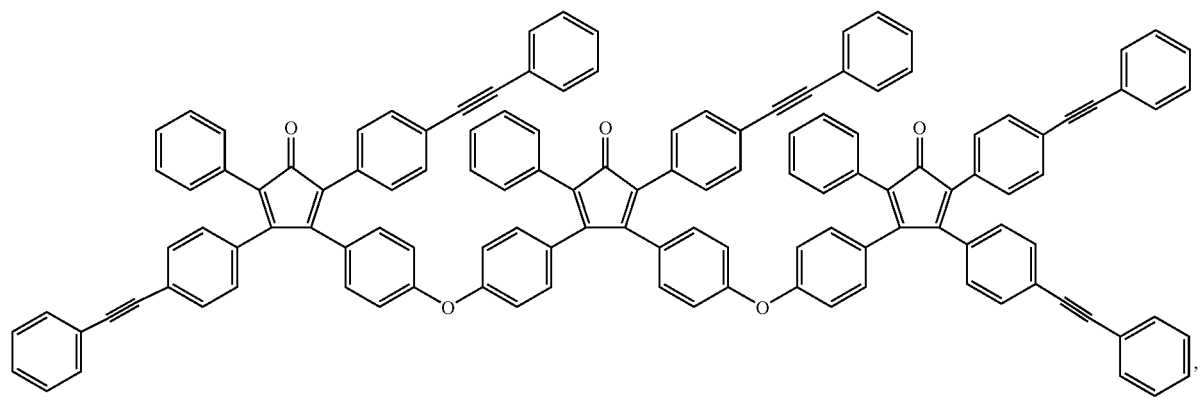
Formula XXIII:
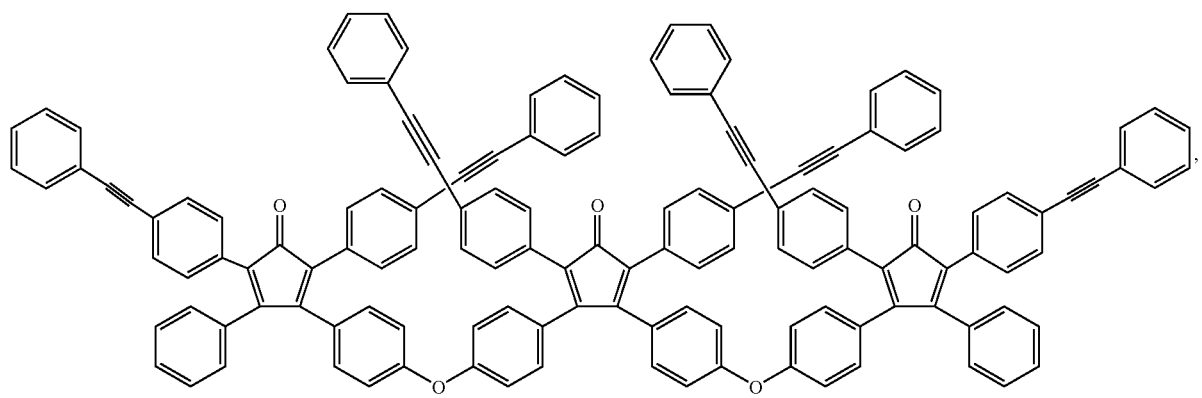
Formula XXIV:
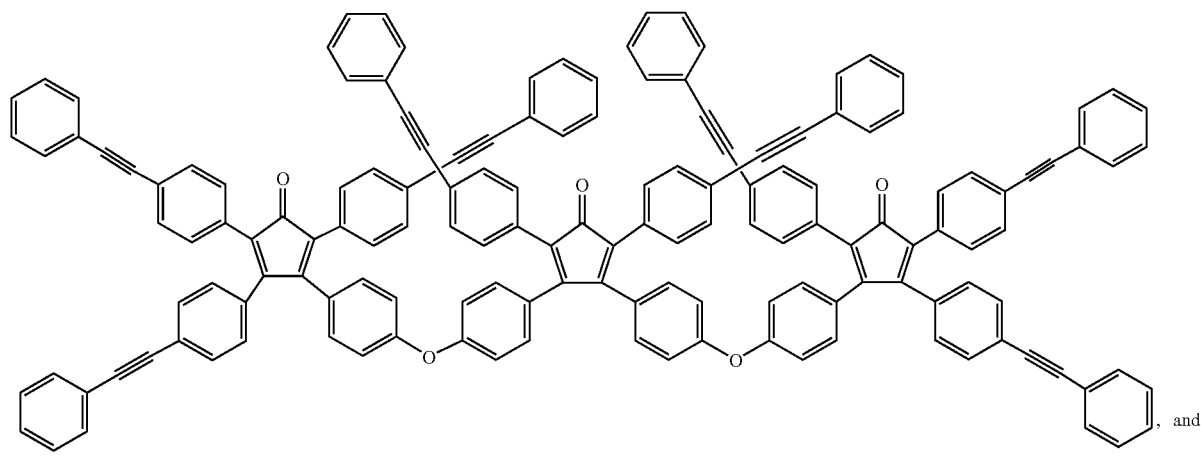
, and

Formula XXV:

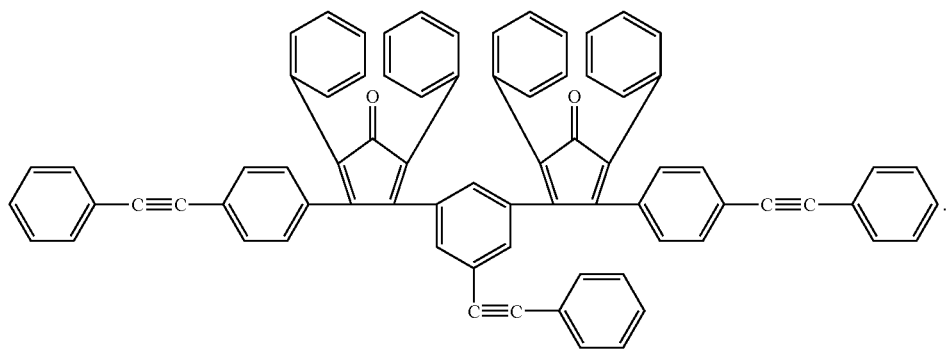

The foregoing monomers I-XXV where the ring structure is a cyclopentadienone may be made, for example, by condensation of substituted or unsubstituted benzils with substituted or unsubstituted benzyl ketones (or analogous reactions) using conventional methods such as those previously disclosed with respect to AxByC'z monomers. Monomers having other structures may be prepared as follows: Pyrones can be prepared using conventional methods such as those shown in the following references and references cited therein: Braham et. al., *Macromolecules* (1978), 11, 343; Liu et. al., *J. Org. Chem.* (1996), 61, 6693-99; van Kerckhoven et. al., *Macromolecules* (1972), 5, 541; Schilling et. al. *Macromolecules* (1969), 2, 85; and Puetter et. al., *J. Prakt. Chem.* (1951), 149, 183. Furans can be prepared using conventional methods such as those shown in the following references and references cited therein: Feldman et. al., *Tetrahedron Lett.* (1992), 47, 7101, McDonald et. al., *J. Chem. Soc. Perkin Trans.* (1979), 1 1893. Pyrazines can be prepared using methods such as those shown in Turchi et. al., *Tetrahedron* (1998), 1809, and references cited therein.

In a preferred embodiment of the invention employing mixtures of the present monomers and other monomers as previously disclosed, it is desirable to maintain a ratio of the corresponding A-functionality and B-functionality in the mixture such that the ratio of B-functional groups to A-functional groups in the reaction mixture is in the range of 1:10 to 10:1, and most preferably from 2:1 to 1:4. It is further desirable to maintain a ratio of A-functional groups to C'-functional groups in the reaction mixture is in the range of 1:1 to 10:1, and most preferably from 2:1 to 10:1. Preferably, the composition additionally comprises a solvent and optionally may also comprise a poragen.

Suitable poragens for use herein include any compound that can form small domains in a matrix formed from the monomers and which can be subsequently removed, for example by thermal decomposition. Preferred poragens are polymers including homopolymers and interpolymers of two or more monomers including graft copolymers, emulsion polymers, and block copolymers. Suitable thermoplastic materials include polystyrenes, polyacrylates, polymethacrylates, polybutadienes, polyisoprenes, polyphenylene oxides, polypropylene oxides, polyethylene oxides, poly(dimethylsiloxanes), polytetrahydrofurans, polyethylenes, polycyclohexylethylenes, polyethyloxazolines, polyvinylpyridines, polycaprolactones, polylactic acids, copolymers of the monomers used to make these materials, and mixtures of these materials. The thermoplastic materials may be linear, branched, hyperbranched, dendritic, or star-like in nature.

The poragen may also be designed to react with the cross-linkable matrix precursor or oligomer during or subsequent to b-staging to form blocks or pendant substitution of the polymer chain. For example, thermoplastic polymers containing reactive groups such as vinyl, acrylate, methacrylate, allyl, vinyl ether, maleimido, styryl, acetylene, nitrile, furan, cyclopentadienone, perfluoroethylene, BCB, pyrone, propiolate, or ortho-diacetylene groups can form chemical bonds with the cross-linkable matrix precursor or oligomer, especially with C' functionality thereof.

The poragen is desirably a material that, upon removal, results in formation of voids or pores in the matrix having an average pore diameter from 1 to 200 nm, more preferably from 2 to 100 nm, most preferably from 5 to 50 nm. Suitable block copolymer poragens include those wherein one of the blocks is compatible with cross-linked polymer matrix resin and the other block is incompatible therewith. Useful polymer blocks can include polystyrenes such as polystyrene and poly-α-methylstyrene, polyacrylonitriles, polyethylene oxides, polypropylene oxides, polyethylenes, polylactic acids, polysiloxanes, polycaprolactones, polyurethanes, polymethacrylates, polyacrylates, polybutadienes, polyisoprenes, polyvinyl chlorides, and polyacetals, and amine-capped alkylene oxides (commercially available as Jeffamine™ polyether amines from Huntsman Corp.).

Preferably, the matrix precursor or oligomer is chemically bound or grafted to the poragen. This may be accomplished by adding functionalized poragens to the monomer prior to b-staging at a time when functional groups on the poragen or the poragen forming monomer itself are available to react with C' functionality on the monomers. Alternatively, some b-staging may occur prior to addition of the poragen and the poragen may be grafted to the oligomer by subjecting the mixture to conditions sufficient to cause a grafting reaction to occur or to otherwise cause residual functional groups on the poragen to react with C' groups in the b-staged reaction product. The mixture is then coated onto a substrate (preferably solvent coated as for example by spin coating or other known methods). The matrix is cured and the poragen is removed, preferably by heating to a temperature above the thermal decomposition temperature of the poragen. Porous films prepared in this manner are useful in making integrated circuit articles where the film separates and electrically insulates conductive metal lines from each other.

Highly preferred poragens are crosslinked polymers made by solution or emulsion polymerization. Such polymerization techniques are known in the art, for example, EP-A-1,245, 586, and elsewhere. Very small crosslinked hydrocarbon based polymer particles have been prepared in an emulsion polymerization by use of one or more anionic-, cationic-, or non-ionic surfactants. Examples of such preparations may be found in *J. Dispersion Sci. and Tech.* vol. 22, No. 2-3, 231-244 (2001); "The Applications of Synthetic Resin Emulsions", H. Warson, Ernest Benn Ltd., 1972, p. 88; *Colloid Polym. Sci.,* 269, 1171-1183 (1991), *Polymer. Bull.,* 43, 417-424 (1999), PCT 03/04668, filed Feb. 12, 2003 and U.S. Ser. No. 10/366, 494, filed Feb. 12, 2003, among other sources.

In addition, small, uniformly dispersed poragens may be formed in situ, by polymerization of one or more addition polymerizable monomers, telegens or graft forming comonomers with the C' functionality of the monomer or a b-stage oligomer of the invention. In this embodiment, the size of the resulting bound poragens can be controlled by limiting the amount of comonomer that is allowed to react with the AxByC'z monomer or oligomer thereof. This results in uniform, extremely small poragens in the resin, and uniform, extremely small pores (nanopores) in the vitrified resin matrix. In both of the foregoing procedures, an oligomeric or polymeric moiety is chemically bound by means of C' functionality, prior to, simultaneously with, or after cross-linking of the invented compounds.

Porous Matrix from AxByC'z Monomers and Oligomers

In the present invention, the C' functionality provides a template that directs placement of bound poragens resulting in uniform, homogeneous porosity in the resulting vitrified resins. For example, a mixture of $A_2B_2C'_2$ monomer and an poragen forming compound such as an addition polymerizable monomer, may be mixed in a suitable solvent and b-staged at moderately elevated temperature to form oligomeric products grafted with in situ prepared polymeric, bound poragens. The resulting precursor may be coated onto the surface of an article such as a microelectronic device and heated to vitrify the oligomer, thereby fixing the desired nanostructure. Subsequently to or simultaneously with the vitrification, the bound poragen may be removed leaving the desired, highly uniform, porous structure.

Desirably, the bound poragen is selected so that a porous, closed cell structure is obtained wherein the pore domains are from 10 to 20 nm in average diameter and not interconnected. The nature of the addition polymerizable monomer, telegen, or graftable monomer utilized to prepare the bound poragen is chosen based on a number of factors, including the size and shape of the pore to be generated, the method of poragen decomposition, the level of any poragen residue permitted in the porous nanostructure, and the reactivity or toxicity of any decomposition products formed. It is also important that the matrix have enough crosslinking density to support the resulting porous structure.

In particular, the temperature at which pore formation occurs should be carefully chosen to be sufficiently high to permit prior solvent removal and at least partial vitrification of the b-staged oligomer, but below the glass temperature, Tg, of the vitrified matrix. If pore formation takes place at a temperature at or above the Tg of the matrix, partial or full collapse of the pore structure may result.

Examples of suitable bound poragens for use herein include moieties having different macromolecular architectures (linear, branched, or dendritic) and different chemical identities, including polyacrylates, polymethacrylates, polybutadiene, polyisoprenes, polypropylene oxide, polyethylene oxide, polyesters, polystyrene, alkyl-substituted polystyrene, and all copolymer combinations, including block copolymers, and functionalized derivatives thereof. Preferably, substances used to prepare bound poragens have one or more functional groups to react with C' groups in the AxByC'z monomer or oligomer. Suitable functionalized polymeric substances include, vinyl capped polystyrene, vinyl capped crosslinked polystyrene copolymers, vinyl capped polystyrene bottlebrush, and vinyl capped polystyrene star shaped polymers. Most preferably, the bound poragen forming compound is a crosslinked vinyl aromatic microemulsion particle (MEP) containing addition polymerizable vinyl functional groups.

MEPs are intramolecularly crosslinked molecular species of extremely small particle size possessing a definable surface of approximately spherical shape. Highly desirably, the MEP's have an average particle size from 5 to 100 nm, most preferably from 5 to 20 nm. Preferably, the MEP is functionalized with an addition polymerizable group such as vinyl group, allowing for ready incorporation into the AxByC'z monomer or oligomer. Desirably the grafting level of the functionalized MEP is sufficient to result in self-alignment, thereby resulting in discrete microphase separation of the MEP's. Upon thermal treatment, the MEP phase may decompose while cross-linking of A and B functionality of the monomer proceeds, thereby forming cross-linked oligomers or vitrified solids with homogeneously distributed nanosize voids in a single step.

Alternatively, the bound poragen can be prepared by reaction of C' functionality, especially ethylenic unsaturation, with an addition polymerizable monomer or telegen to form a grafted polymer. An example is the reaction of a vinyl capped polystyrene, polyacrylate, or polymethacrylate, or a vinyl capped oligomer thereof with the AxByC'z monomer or oligomer to make a block structure as shown in following scheme where m and n are integers greater than or equal to one:

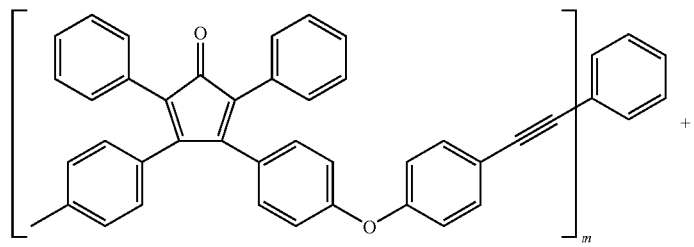

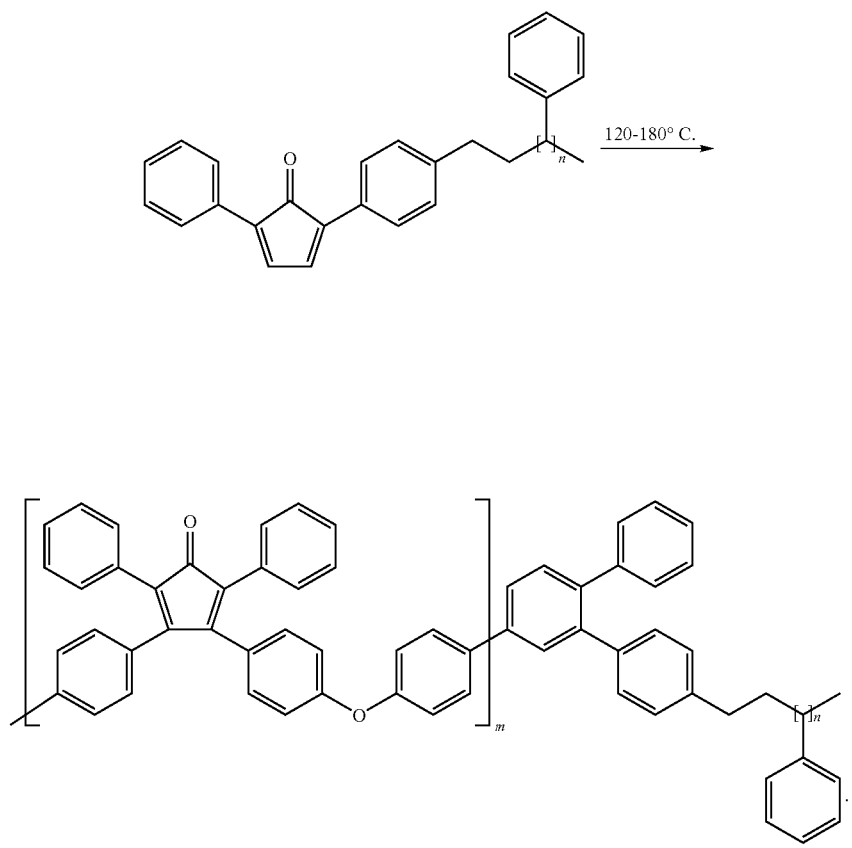

XXVI

The result of incorporating bound poragens into the matrix during its formation in the foregoing manners is a near uniform correspondence of pores with initial bound poragen moieties and limited or no agglomeration and heterogeneous phase separation of the poragens. In addition, separate thermal processing for purposes of pore formation may be avoided if the decomposition temperature of the bound poragen is appropriately chosen. The resultant articles, including films or coatings, are extremely low dielectric constant, nanoporous materials having highly uniform electrical properties due to the uniformity of pore distribution.

Highly desirably, the matrix materials formed from monomers of the present invention are relatively thermally stable at temperatures of at least 300° C., preferably at least 350° C. and most preferably at least 400° C. In addition, the matrix polymer also has a Tg of greater than 300° C. and more preferably greater than 350° C. after being fully crosslinked or cured. Further desirably, the crosslinking or vitrification temperature of the invention, defined as the temperature upon heating at which flexural modulus increases most quickly, is desirably below the decomposition temperature of the poragen, preferably less than or equal to 400° C., most preferably, less than or equal to 300° C. This property allows crosslinking to take place before substantial pore formation occurs, thereby preventing collapse of the resulting porous structure. The C' groups contained in the monomers of the present invention contribute to an enhanced rate of crosslinking at lower temperatures versus monomers containing only A and B functional groups. This in turn provides a beneficial increase in the rate of flexural modulus development. Finally, in a desirable embodiment of the invention, the flexural modulus of the partially crosslinked and cured polymer, either with or without poragen present, desirably reaches a maximum at temperatures less than or equal to 400° C., preferably less than or equal to 350° C., and most preferably, less than or equal to 300° C. and little or no flexural modulus loss occurs upon heating the fully cured matrix to a temperature above 300° C., such as may be encountered during pore formation via thermolysis.

In one suitable method of operation, AxByC'z monomer, the optional functionalized MEP or other poragen forming material, optional comonomer, and optional solvent are combined and heated at elevated temperature, preferably at least 160° C., more preferably at least 200° C. for at least several hours, more preferably at least 24 hours to make a solution of crosslinkable b-staged oligomers optionally bearing bound poragens. The amount of matrix precursor or monomer, relative to the amount of poragen forming compound may be adjusted to give a cured matrix having the desired porosity. Preferably, the amount of poragen forming compound based on combined poragen and monomer weight is from 5 to 80 percent, more preferably from 20 to 70 percent, and most preferably from 30 to 60 percent.

Solutions containing monomer and poragen forming compound for use herein desirably are sufficiently dilute to result in optical clear solutions having the desired coating and application properties. Preferably, the amount of solvent employed is in the range of 50-95 percent based on total solution weight.

The solution may be applied to a substrate by any suitable method such as spin coating, and then heated to remove most of the remaining solvent and leave the monomer or b-staged oligomer, optionally containing bound poragen moieties dispersed therein. During the solvent removal process and/or during subsequent thermal processing, the poragen phase desirably forms separate uniformly dispersed occlusions within the matrix precursor or fully cured matrix. Upon continued or subsequent heating, the occlusions decompose into decomposition products that may diffuse through the cured matrix, thereby forming a porous matrix.

The concentration of pores in above porous matrix is sufficiently high to lower the dielectric constant or reflective index of the cured polymer, but sufficiently low to allow the resulting porous matrix to withstand the process steps required in the fabrication of microelectronic devices. Preferably, the quantity of pores in the resulting cross-linked porous matrix is sufficient to result in materials having a dielectric constant of less than 2.5, more preferably less than 2.0.

The average diameter of the pore is preferably less than 100 nm, more preferably less than 20 nm, and most preferably less than 10 nm. The pore sizes can be easily controlled by adjusting the size of the poragen employed in a grafting process or adjusting the quantity of addition polymerizable monomer or telegen employed in production of the bound poragen.

The compositions of the invention may be used to make dielectric films and interlayer dielectrics for integrated circuits in accordance with known processes, such as those of U.S. Pat. No. 5,965,679. To make a porous film the bound poragen is preferably removed by thermal decomposition of the poragen.

The invention is further illustrated by the following Examples that should not be regarded as limiting of the present invention. Unless stated to the contrary or conventional in the art, all parts and percents are based on weight.

Example of $A_2B_2C'_4$ Monomer

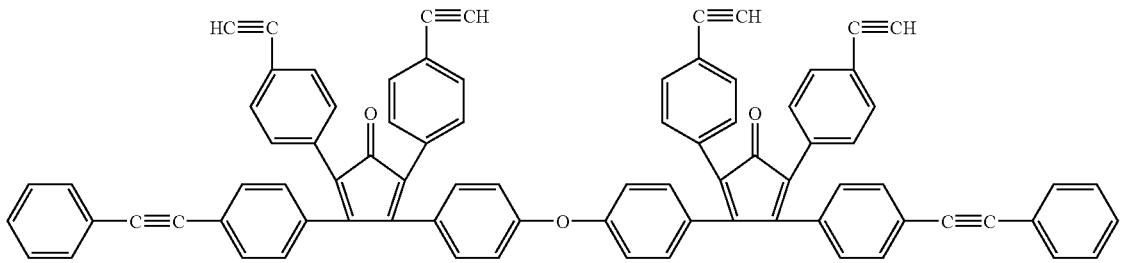

This monomer may be prepared via (a) Friedel-Crafts diacylation of diphenyl oxide with 4-bromophenylacetyl chloride to provide 4,4'-bis[(4-bromophenyl)acetyl]phenyl ether (b) modified Kornblum oxidation of 4,4'-bis[(4-bromophenyl)acetyl]phenyl ether to 4,4'-bis[(4-bromophenyl)glyoxalyl]phenyl ether, then (c) bis(phenylation) of 4,4'-bis[(4-bromophenyl)-glyoxalyl]phenyl ether to provide 4,4'-bis[(4-phenylethynylphenyl)glyoxalyl]phenyl ether. This provides the bis(phenylethynyl)tetraketone used to prepare the monomer. The second component, 1,3-bis(4-ethynylphenyl)-2-propanone, is prepared via modified Heck reaction of 1,3-bis (4-bromophenyl)-2-propanone with (trimethylsilyl) acetylene followed by treatment of the resultant 1,3-bis[4-(trimethylsilyl)ethynyl]-2-propanone with potassium carbonate to provide the corresponding 1,3-bis(ethynylphenyl)-2-propanone. Double Aldol condensation of one equivalent of 4,4'-bis[(4-phenylethynylphenyl)glyoxalyl]phenyl ether with two equivalents of 1,3-bis(4-ethynylphenyl)-2-propanone in the presence of a basic-acting catalyst provides the $A_2B_2C'_4$ monomer. It is also operable to condense of one equivalent of 4,4'-bis[(4-phenylethynylphenyl)glyoxalyl] phenyl ether with two equivalents of 1,3-bis[4-(trimethylsilyl)ethynylphenyl]-2-propanone Example of A$_4$B$_2$C'$_7$ Monomer

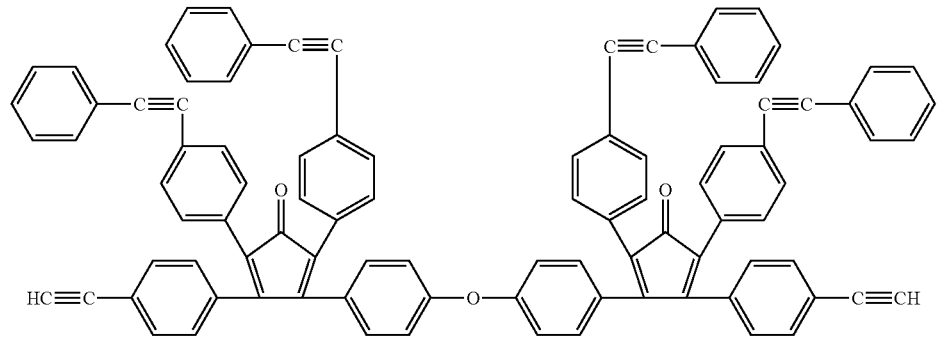

This monomer may be prepared via repeating steps (a), (b) and (c), then (d) bis(ethynylation) of 4,4'-bis[(4-bromophenyl)glyoxalyl]phenyl ether to first provide 4,4'-bis[(4-(trimethylsilyl)ethynylphenyl)glyoxalyl]phenyl ether, then 4,4'-bis[(4-ethynylphenyl)glyoxalyl]phenyl ether after treatment with potassium carbonate (see Example 1, herein). This provides the bis(ethynyl)tetraketone used to prepare the monomer. The second component, 1,3-bis(4-phenylethynylphenyl)-2-propanone, is prepared via bis(phenylethynylation) of 1,3-bis(4-bromophenyl)-2-propanone with phenylacetylene using the modified Heck reaction. Double Aldol condensation of one equivalent of 4,4'-bis[(4-ethynylphenyl)glyoxalyl]phenyl ether with two equivalents of 1,3-bis(4-phenylethynylphenyl)-2-propanone in the presence of a basic-acting catalyst provides the A$_4$B$_2$C'$_2$ monomer. It is also operable to condense of one equivalent of 4,4'-bis[(4-(trimethylsilyl)ethynylphenyl)glyoxalyl]phenyl ether with two equivalents of 1,3-bis[4-phenylethynylphenyl]-2-propanone.

Example of A$_4$B$_2$C' Monomer provide 1,3-bis[(phenyl)acetyl]-5-bromobenzene (b) modified Kornblum oxidation of 1,3-bis[(phenyl)acetyl]-5-bromobenzene to 1,3-bis[(phenyl)glyoxalyl]-5-bromobenzene, then (c) modified Heck reaction of 1,3-bis[(phenyl)glyoxalyl]-5-bromobenzene with (trimethylsilyl)acetylene followed by treatment of the resultant 1,3-bis[(phenyl)glyoxalyl]-5-(trimethylsilyl)ethynylbenzene with potassium carbonate to provide the corresponding 1,3-bis[(phenyl)glyoxalyl]-5-ethynylbenzene. This provides the ethynyltetraketone used to prepare the monomer. The second component, 1,3-bis(4-phenylethynylphenyl)-2-propanone, is prepared as previously delineated herein for the synthesis of the A$_4$B$_2$C'$_2$ monomer. Double Aldol condensation of one equivalent of 1,3-bis[(phenyl)glyoxalyl]-5-ethynylbenzene with two equivalents of 1,3-bis(4-phenylethynylphenyl)-2-propanone in the presence of a basic-acting catalyst provides the A$_4$B$_2$C' monomer. It is also operable to condense of one equivalent of 1,3-bis[(phenyl)glyoxalyl]-5-(trimethylsilyl)ethynylben-

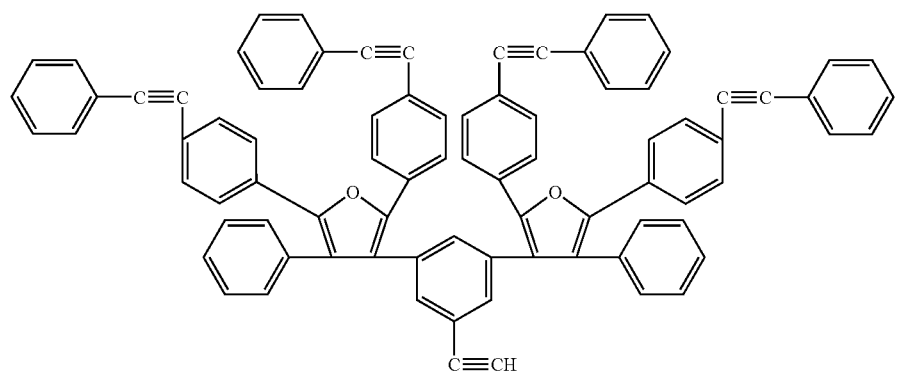

This monomer may be prepared via (a) Friedel-Crafts acylation of benzene with 5-bromophenyldiacetyl chloride to zene with two equivalents of 1,3-bis(4-phenylethynylphenyl)-2-propanone.

EXAMPLE 1

Synthesis of $A_2B_2C'_2$ Monomer

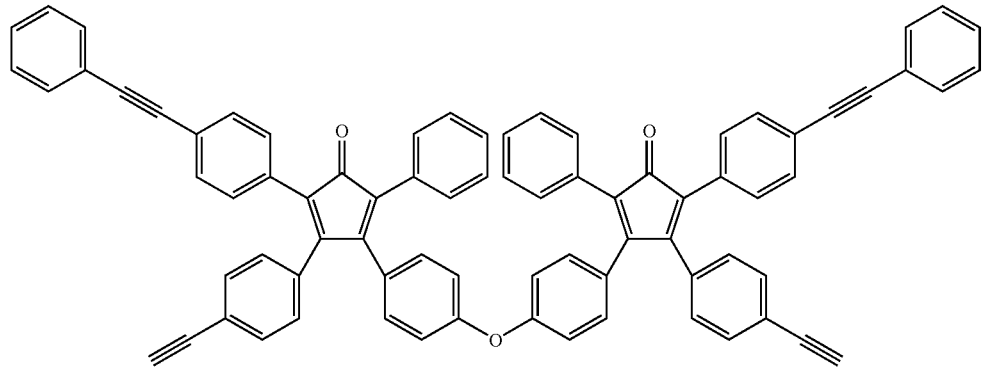

A) Synthesis of 4,4'-bis[(4-(trimethylsilyl)ethynylphenyl)glyoxalyl]phenyl ether N,N-dimethylformamide (110.8 grams) which has been sparged with dry nitrogen, triphenylphosphine (0.36 gram, 0.00137 mole) and palladium (II) acetate (0.096 gram, 0.00043 mole) are added in the indicated order under a dry nitrogen atmosphere to a one liter glass three neck round bottom reactor. The reactor is outfitted with a Claisen adaptor, an addition funnel, a fan cooled spiral condenser, a thermometer with thermostatically controlled heating mantle, and a magnetic stirrer. Stirring is commenced at 22° C. with maintenance of the dry nitrogen atmosphere. After 85 minutes at this temperature, the following reactants are charged to the stirred reaction mixture in the order indicated: 4,4'-bis[(4-bromophenyl)glyoxalyl]phenyl ether (17.8 grams, 0.03 mole), a rinse of 79.2 grams of the N,N-methylformamide, triethylamine (15.0 grams, 0.148 mole) which has been sparged with dry nitrogen, and (trimethylsilyl)acetylene (3.10 grams, 0.0316 mole). Additional (trimethylsilyl)acetylene (17.5 grams, 0.178 mole) is added to the addition funnel on the reactor. Heating is commenced and after 8 minutes a temperature of 41° C. is achieved and a clear light yellow colored solution forms. After a cumulative reaction time of 35 minutes, a temperature of 80° C. is achieved, and dropwise addition of (trimethylsilyl)acetylene over a period of 48 minutes is commenced. Two hours after completion of the dropwise addition of the phenylacetylene at 80° C., high pressure liquid chromatographic (HPLC) analysis reveals that full conversion of the 4,4'-bis[(4-bromophenyl)glyoxalyl]phenyl ether reactant to a single product has occurred. The crude bis((trimethylsilyl)ethynylation) reaction product is allowed to cool to room temperature (23.5° C.), and deionized water (66 milliliters) is added dropwise to the stirred reaction mixture. After completion of the deionized water addition, the product separates in the form of yellow colored crystals slurried in amber colored liquid. The slurry is vacuum filtered onto a coarse fritted glass funnel, the recovered product dissolved into dichloromethane (100 milliliters) and then washed twice in a separatory funnel with portions of deionized water (50 milliliters). The solution is filtered through a bed of anhydrous magnesium sulfate powder packed on a fritted glass funnel, then dried in the vacuum oven at 50° C. to a constant weight of 19.3 grams of an amber colored crystalline solid (100 percent apparent isolated yield). HPLC analysis of the product demonstrated 100 area percent purity.

B) Synthesis of 4,4'-bis[(4-ethynylphenyl)glyoxalyl]phenyl ether 4,4'-Bis[(4-(trimethylsilyl)ethynylphenyl)glyoxalyl]phenyl ether (19.3 grams, 0.03 mole) is added to a one liter glass three neck reactor, then dissolved under a dry nitrogen atmosphere into anhydrous toluene (100 milliliters) which has been sparged with dry nitrogen. Anhydrous methanol (200 milliliters) which has been sparged with dry nitrogen is added to the magnetically stirred solution in toluene, followed by the addition of anhydrous potassium carbonate (0.83 gram, 6.0 mmole). The reactor is outfitted with a fan cooled spiral condenser, a thermometer and magnetic stirrer. Stirring is commenced at 23.8° C.) with maintenance of the dry nitrogen atmosphere. After 2 hours reaction, HPLC analysis reveals that full conversion of the 4,4'-bis[(4-(trimethylsilyl)ethynylphenyl)glyoxalyl]phenyl ether reactant to a single product has occurred. The crude bis(ethynylation) reaction product is rotary evaporated under reduced pressure at 50° C. to provide 21.8 grams of brown colored solid. Further purification is completed by dissolving the product into a minimum of dichloromethane followed by chromatography on a column of neutral silica gel using dichloromethane as the eluent. This results in recovery of a light yellow colored effluent from the column and removal of a dark amber colored product at the origin of the column. After rotary evaporation of the effluent from the chromatographic purification, followed by further drying in the vacuum oven at 50° C., 11.2 grams of a light yellow colored 4,4'-bis[(4-ethynylphenyl)glyoxalyl]phenyl ether are obtained. HPLC analysis demonstrates 98.95 area percent purity for the product (a single minor contaminant peak comprising the balance). Electron impact mass spectroscopic (EI MS) analysis using a direct insertion probe confirms the structure of the product. The intact molecular ion (M+) is clearly observed at m/z=482.

C) Synthesis of Trimethylsilyl Functionalized Monomer

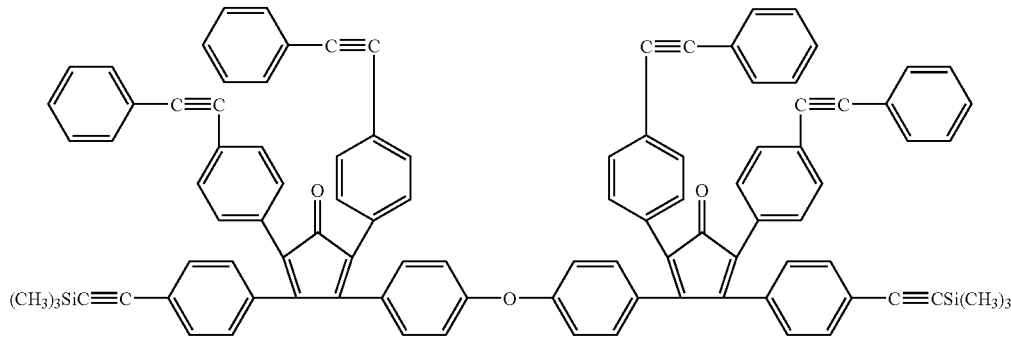

4,4'-bis[(4-(Trimethylsilyl)ethynylphenyl)glyoxalyl]phenyl ether is further purified via dissolution in magnetically stirred hot toluene (75 milliliters) followed by the addition of 2-propanol (200 milliliters), then deionized water (25 milliliters). After stirring ceased and upon cooling of the solution to room temperature, a black tar precipitates and is removed via decantation. Rotary evaporation of the decanted liquid provides a yellow crystalline product.

A portion (0.94 gram, 1.5 mmole) of this purified 4,4'-bis[(4-(trimethylsilyl)ethynyl-phenyl)glyoxalyl]phenyl ether, 1,3-bis(4-phenylethynylphenyl)-2-propanone (1.26 grams, 3.07 mole), 2-propanol (21.5 milliliters) and toluene (14.3 milliliters), are added to a 250 milliliter three neck round bottom reactor. The reactor is additionally outfitted with a chilled (2° C.) condenser, a thermometer with thermostatically controlled heating mantle, a Claisen adaptor, a septum covered inlet, a nitrogen sparge tube, and a magnetic stirrer. A syringe is charged under a dry nitrogen atmosphere with phosphazene base $P_2$—Et {[1-ethyl-2,2,4,4,4-pentakis(dimethylamino)$2\lambda^5,4\lambda^5$-catenadi(phosphazene)]} (0.026 milliliters) diluted into 2-propanol (0.5 milliliter). Stirring and heating under a nitrogen atmosphere are commenced and once 72° C. is achieved, a clear solution forms and sparging with nitrogen (0.25 liter per minute) is initiated. After 23 minutes, the temperature is stabilized at 75° C. and the sparge tube is removed and replaced with the overhead inlet for nitrogen. The phosphazene base solution in 2-propanol is injected through the septum on the reactor causing the yellow colored solution to immediately turn dark red in color. After 104 minutes of reaction at 75° C., a sample removed for HPLC analysis reveals that full conversion of the 4,4'-bis[(4-(trimethylsilyl)ethynyl-phenyl)glyoxalyl]phenyl ether has occurred, concurrent with a minor amount of unreacted 1,3-bis(4-phenylethynylphenyl)-2-propanone. After an additional 14 minutes, heating is discontinued, the heating mantle is removed from the reactor and additional 2-propanol (75 milliliters) is added to the reactor. The reaction mixture is cooled using a cooling fan on the reactor exterior and when the stirred slurry reaches 28° C., the product is recovered via vacuum filtration through a coarse fritted glass funnel. The crystalline product is pressed into a cake and then washed on the funnel with additional 2-propanol until the filtrate is clear. After drying in a vacuum oven at 60° C., 1.85 grams (89.7 percent isolated yield) of monomer product is recovered as a dark purple red colored crystalline powder. The product is found to have a purity of 98.0 percent by HPLC analysis.

D) Monomer Synthesis

A portion (1.72 gram, 1.25 mmole) of the silane compound from Step C) is added to a 250 milliliter glass three neck reactor, then dissolved under a dry nitrogen atmosphere into anhydrous toluene (25 milliliters) which has been sparged with dry nitrogen. Anhydrous methanol (50 milliliters) which has been sparged with dry nitrogen is added to the magnetically stirred solution in toluene, followed by the addition of anhydrous potassium carbonate (0.035 gram, 0.25 mmole). The reactor is outfitted with a fan cooled spiral condenser, a thermometer and magnetic stirrer. Stirring is commenced at 22.5° C. with maintenance of the dry nitrogen atmosphere. After 12 hours reaction, the crude reaction product is rotary evaporated under reduced pressure at 50° C. to provide 1.75 grams of dark purple amber colored solid. HPLC analysis of a portion of the product reveals the presence of >50 area percent of the desired monomer product. Further purification is completed by dissolving a portion of the product into a minimum of toluene followed by chromatography on a column of neutral silica gel using toluene as the eluent. This results in recovery of a dark red purple colored effluent from the column and removal of a dark amber colored product at the origin of the column. After rotary evaporation of the effluent from the chromatographic purification, followed by further drying in the vacuum oven at 40° C., the dark purple red colored monomer is recovered in 97.9 percent purity (HPLC analysis).

E) Monomer b-Staging and Cure

Differential scanning calorimetry (DSC) is completed using a 1.4 milligram portion of the monomer from step D). A DSC 2910 Modulated DSC (TA Instruments) is employed, using a heating rate of 7° C. per minute from 25° C. to 500° C. under a stream of nitrogen flowing at 45 cubic centimeters per minute. A slight endothermic transition is observed with a minimum at 77.0° C. (3.2 joules per gram). An exothermic transition, tentatively attributed to reaction of cyclopentadienone groups with ethynyl groups and with phenylethynyl groups, is observed with a maximum at 151.2° C. followed by a second shoulder maximum at 167.7° C. (159.4 joules per gram). The onset temperature for this exothermic transition is 93.4° C., while the ending temperature is 268.6° C. A second exothermic transition, predominately attributed to reaction of phenylethynyl groups with phenylethynyl groups, is observed with a maximum at 395.6° C. (62.1 joules per gram). This exothermic transition has evidence of a slight shoulder preceding the main peak exotherm and a slight shoulder following the main peak exotherm. The onset temperature for this exothermic transition is 337.6° C., while the ending temperature is 481.8° C. The product recovered from the DSC analysis is a tough, hard, golden yellow colored, solid, suitable for use as an insulating dielectric.

What is claimed is:

1. A compound corresponding to the formula,

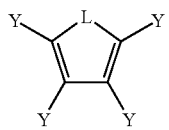

wherein L is —O—, —S—, —N=N—, —C(O)—, —(SO$_2$)—, or —OC(O)—;

Y is independently in each occurrence hydrogen, halogen, an unsubstituted or inertly substituted hydrocarbyl group, Y', or two adjacent Y groups together with the carbons to which they are attached form a fused aromatic ring, Y' is a single covalent bond or a divalent derivative of an unsubstituted or inertly substituted hydrocarbyl group joining two or more divalent remnants of the foregoing structure, and in at least one occurrence, Y is —Y"(—C≡CR$^1$)$_m$, and in at least one other occurrence, Y is —Y"—(C≡CR$^2$)$_n$; or in at least one occurrence, Y is —Y"(—C≡CR$^1$)$_m$(C≡CR$^2$)$_n$; wherein, Y" is a single covalent bond or a polyvalent derivative of an unsubstituted or inertly substituted hydrocarbyl group;

R$^1$ is C$_{6-20}$ aryl;

R$^2$ is hydrogen, C$_{1-6}$ alkyl, C$_{1-6}$ hydroxyalkyl, or trimethylsilyl; and m and n are integers from 1 to 5.

2. A compound corresponding to the formula:

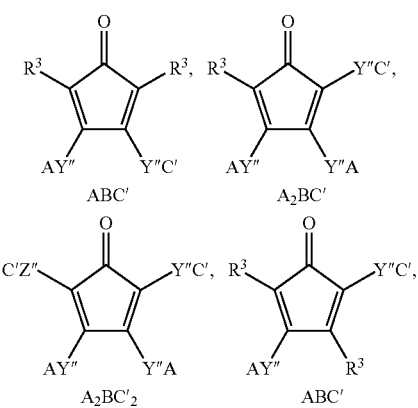

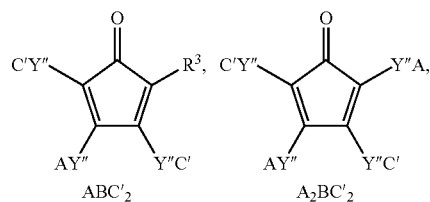

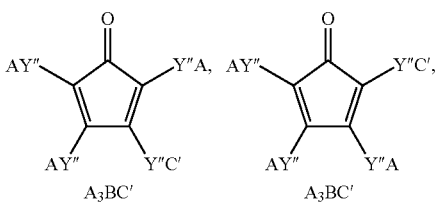

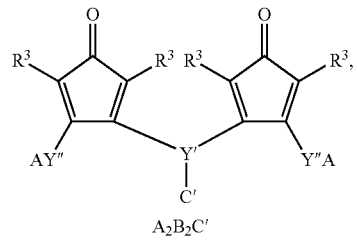

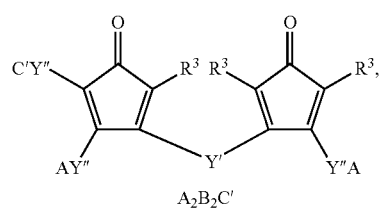

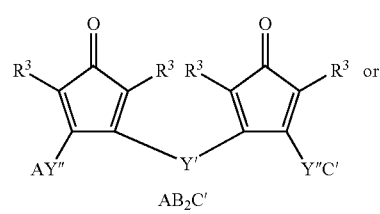

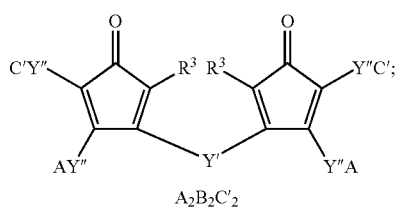

wherein R$^3$ is C$_{6-20}$ aryl or inertly substituted aryl;

C' is —C≡CR$^2$, A is arylethynyl, and Y' and Y" are as defined in claim 1.

3. A compound according to claim 1 wherein R$^1$ is phenyl and R$^2$ is hydrogen at each occurrence.

4. A compound according to claim 3 corresponding to the formula:
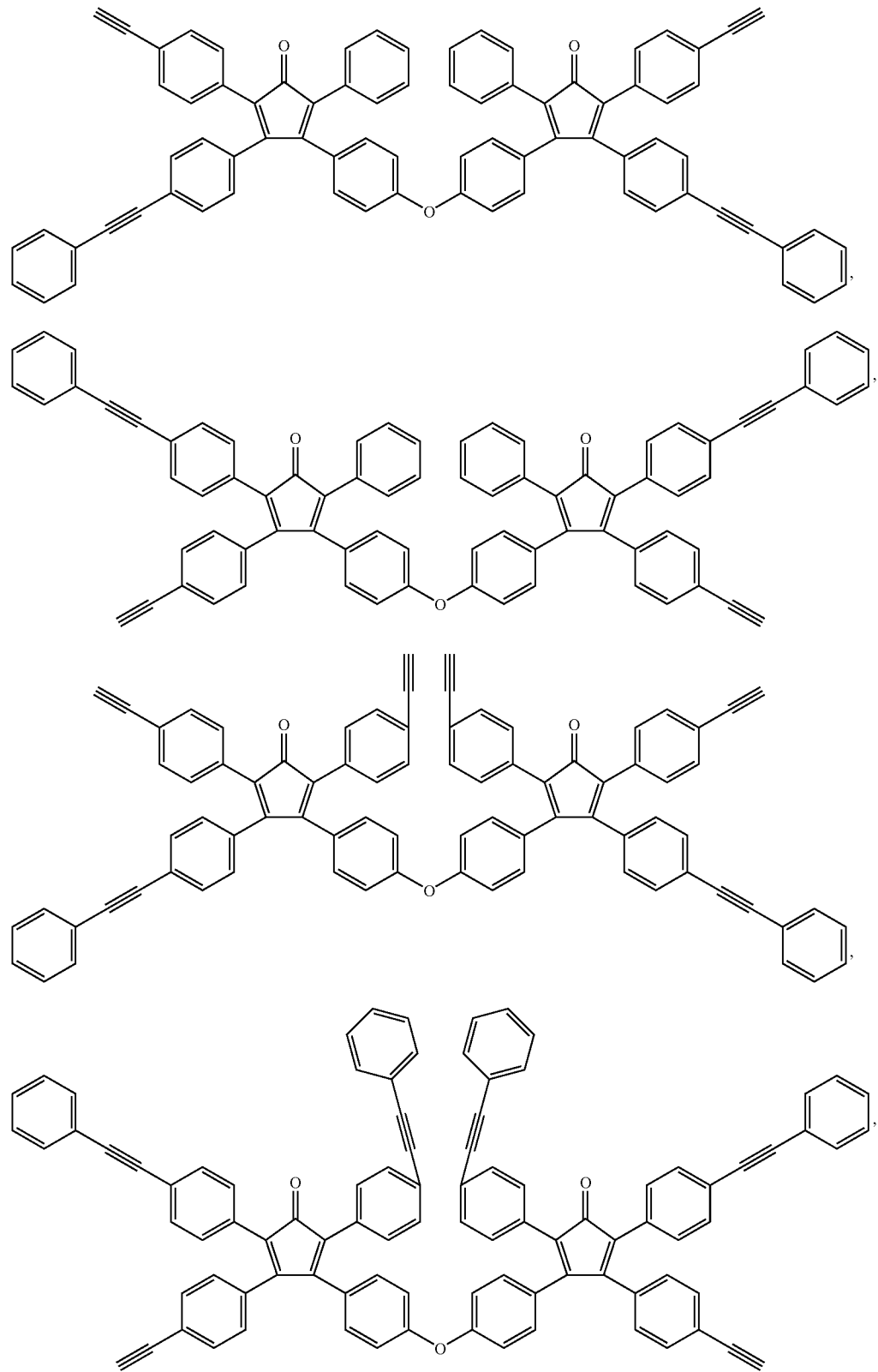

-continued
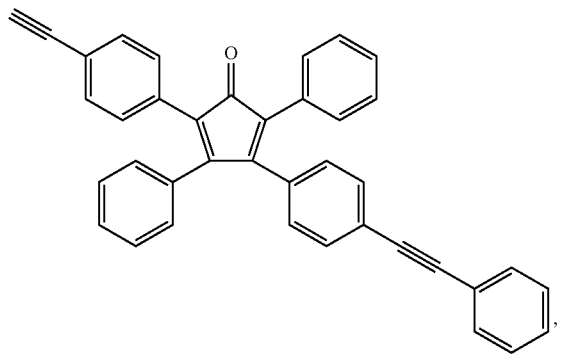
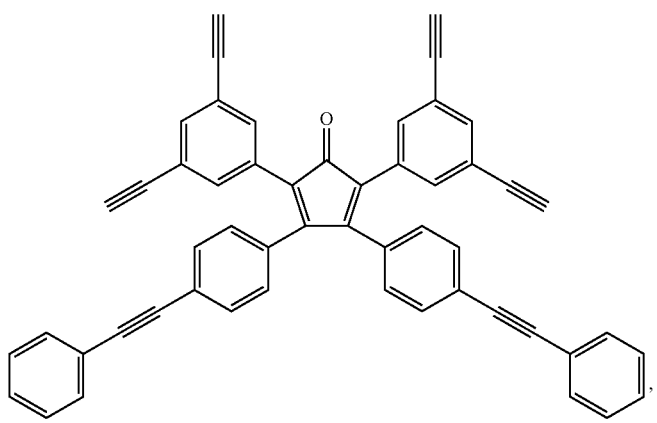
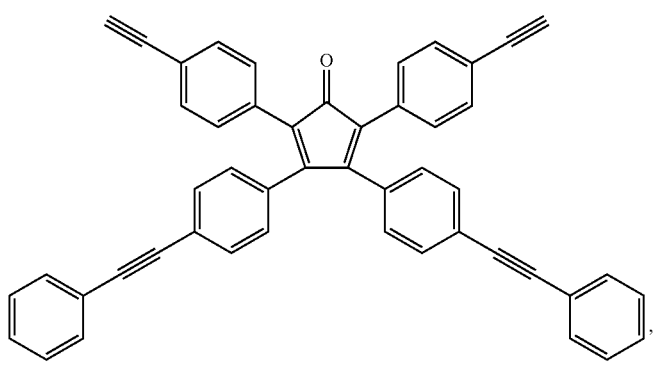
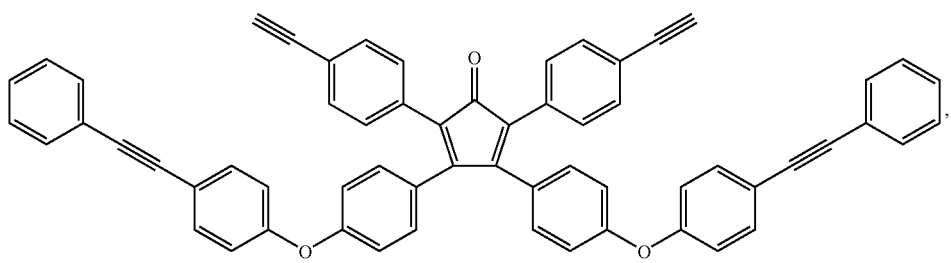

-continued
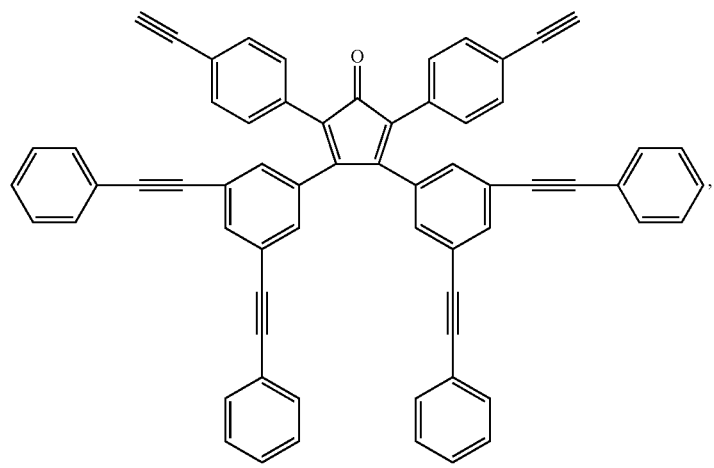
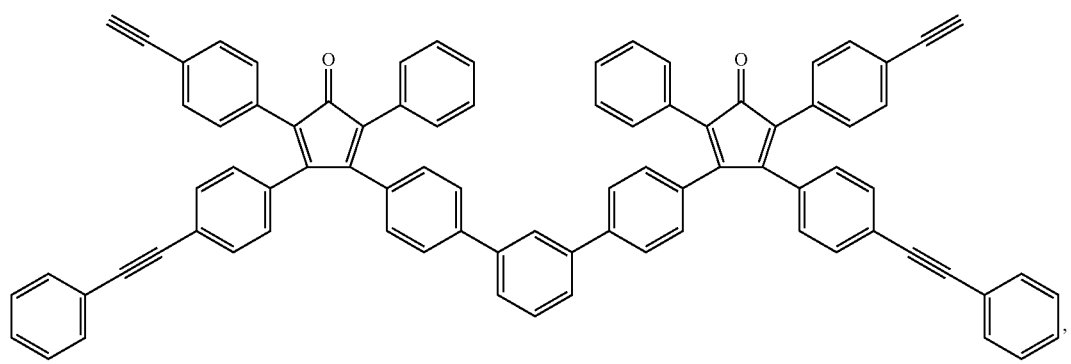
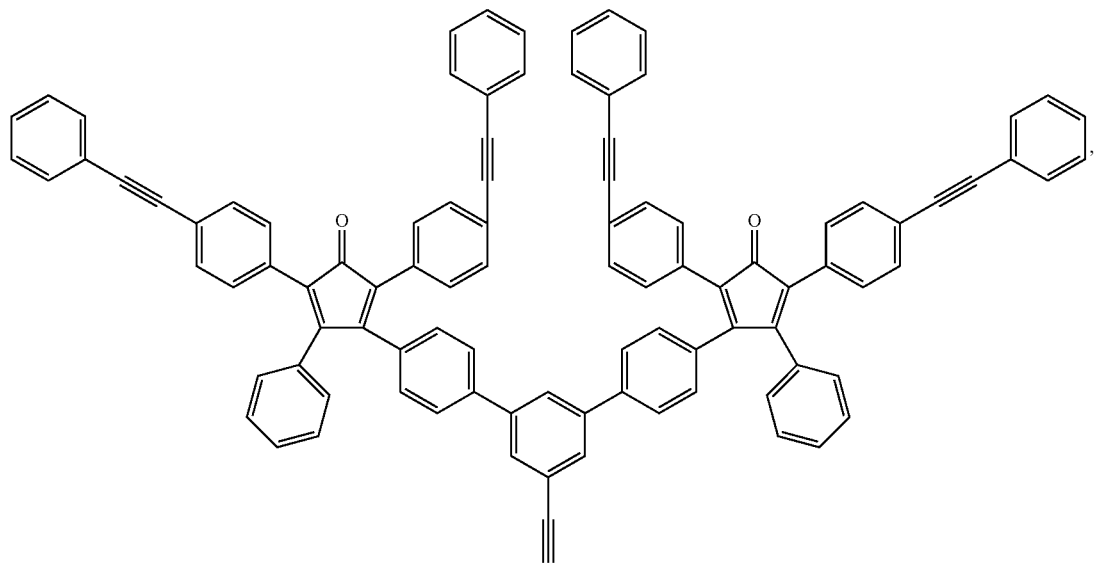

-continued

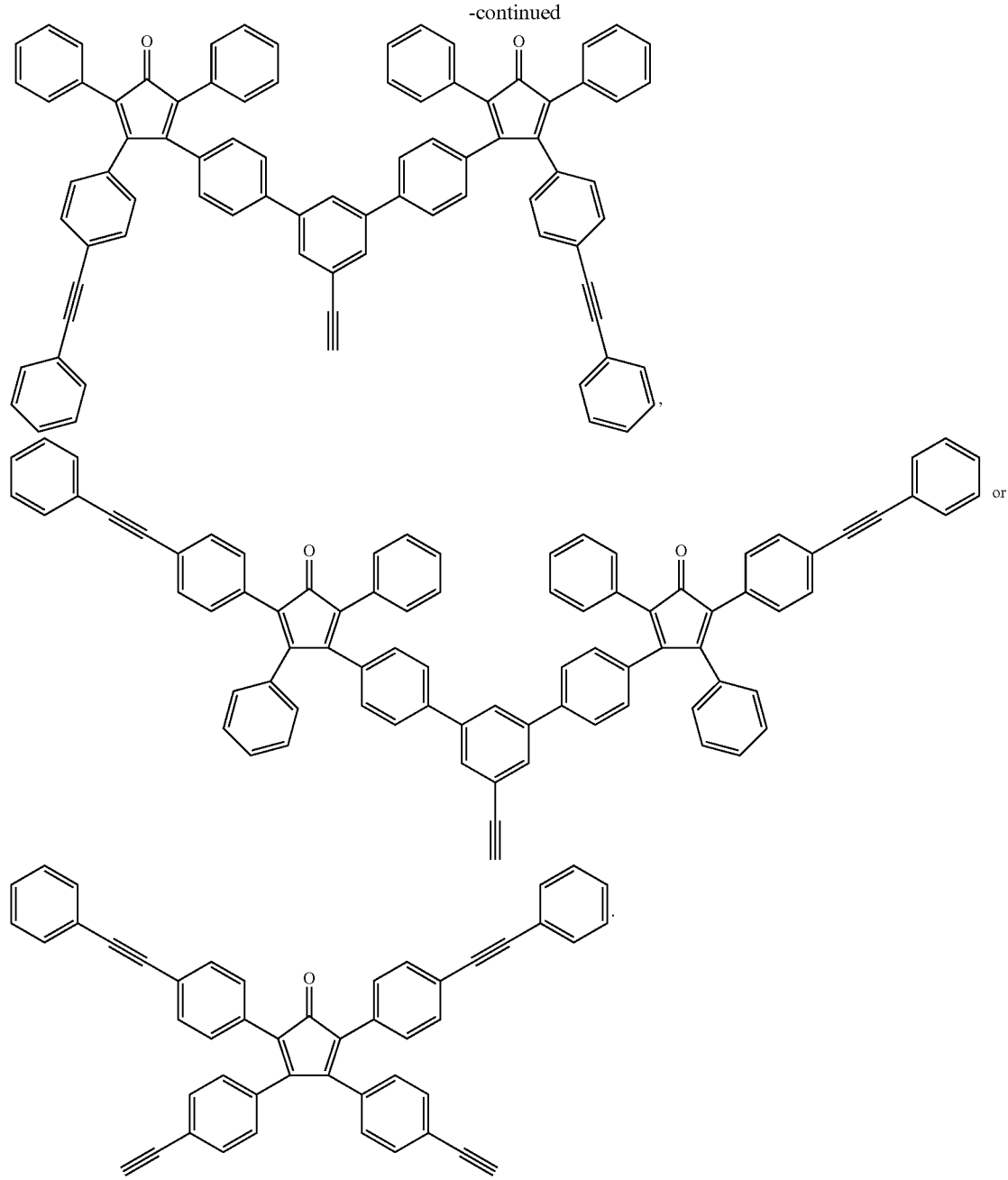

5. A cross-linked polymer formed by curing a composition comprising a compound according to claim 1.

6. A crosslinked polymer formed by curing a composition comprising a compound according to claim 4.

7. A composition comprising a cross-linked polymer according to claim 5 and a poragen.

8. A porous matrix formed by removing the poragen from the cross-linked polymer of claim 7.

* * * * *